(12) United States Patent
Hyde, Jr.

(10) Patent No.: US 6,387,096 B1
(45) Date of Patent: May 14, 2002

(54) MAGNETIC ARRAY IMPLANT AND METHOD OF TREATING ADJACENT BONE PORTIONS

(76) Inventor: Edward R. Hyde, Jr., 450 El Camino Real, #524, Menlo Park, CA (US) 94025

(*) Notice: Subject to any disclaimer, the term of this patent is extended or adjusted under 35 U.S.C. 154(b) by 45 days.

(21) Appl. No.: 09/594,356

(22) Filed: Jun. 13, 2000

(51) Int. Cl.[7] .............................................. A61B 17/68
(52) U.S. Cl. ..................... 606/60; 623/23.49
(58) Field of Search ................. 623/16.11, 23.49; 606/60

(56) References Cited

U.S. PATENT DOCUMENTS

| | | | |
|---|---|---|---|
| 3,820,534 A | * 6/1974 | Kraus et al. | ............ 623/23.49 |
| 4,024,588 A | 5/1977 | Janssen et al. | |
| 4,029,091 A | 6/1977 | von Bezold et al. | |
| 4,038,704 A | 8/1977 | Ring | |
| 4,057,858 A | 11/1977 | Helfet | |
| 4,079,469 A | 3/1978 | Wadsworth | |
| 4,129,902 A | 12/1978 | Harmon | |
| 4,195,367 A | 4/1980 | Kraus | |
| 4,203,216 A | 5/1980 | Deguemp | |
| 4,214,322 A | * 7/1980 | Kraus | ...................... 623/16.11 |
| 4,216,548 A | * 8/1980 | Kraus | ...................... 623/16.11 |
| 4,224,695 A | 9/1980 | Grundei et al. | |
| 4,332,037 A | 6/1982 | Esformes et al. | |
| 4,547,912 A | 10/1985 | Sherva-Parker | |
| 4,741,698 A | 5/1988 | Andrews | |
| 4,743,264 A | 5/1988 | Sherva-Parker | |
| 4,781,720 A | 11/1988 | Sherva-Parker | |
| 4,813,961 A | 3/1989 | Sostegni | |
| 4,871,310 A | 10/1989 | Vardimon | |
| 4,906,189 A | 3/1990 | Knapp | |
| 5,062,855 A | 11/1991 | Rincoe | |
| 5,127,913 A | * 7/1992 | Thomas, Jr. | ................. 606/62 |
| 5,168,183 A | 12/1992 | Whitehead | |
| 5,421,722 A | 6/1995 | Stemmann | |
| 5,425,763 A | * 6/1995 | Stemmann | ................... 623/11 |
| 5,458,558 A | * 10/1995 | Liboff et al. | .................. 600/13 |
| 5,462,054 A | 10/1995 | Rapoport et al. | |
| 5,507,835 A | * 4/1996 | Jore | ............................ 623/36 |
| 5,595,563 A | 1/1997 | Moisdom | |
| 5,611,689 A | 3/1997 | Stemmann | |
| 5,693,054 A | * 12/1997 | Durham et al. | ............... 606/62 |

(List continued on next page.)

OTHER PUBLICATIONS

*Dexter Magnetic Technologies Permanent Magnet Catalog,* Dexter Corporation, Magnetic Technologies, 1998.

Primary Examiner—Jeffrey A. Smith
Assistant Examiner—Michael B. Priddy
(74) Attorney, Agent, or Firm—Pennie & Edmonds LLP

(57) ABSTRACT

The present invention relates to apparatus and methods for stabilizing and or maintaining adjacent bone portions in predetermined desired relationships and for constraining one, two or three-dimensional motion and/or rotation of the adjacent bone portions. More particularly, the present invention relates to a magnetic apparatus with at least two magnetic arrays, each of which may include any number of magnets arranged in a predetermined manner and each magnetic array generating a magnetic field therearound. Once implanted and secured to the adjacent bone portions, the apparatus provides interacting magnetic fields in the area of the bone portions and transduces magnetic energy into mechanical energy and mechanical energy into potential magnetic energy, thereby reproducing functionally anatomic and/or anatomically advantageous arrangement of the bone portions.

14 Claims, 24 Drawing Sheets

U.S. PATENT DOCUMENTS

| | | |
|---|---|---|
| 5,725,597 A | 3/1998 | Hwang |
| 5,814,047 A * | 9/1998 | Emilio et al. ................. 606/62 |
| 5,879,386 A * | 3/1999 | Jore ............................ 623/18 |
| 5,886,609 A | 3/1999 | Stelter |
| 5,894,181 A | 4/1999 | Imlach |
| 5,929,546 A | 7/1999 | Lambert |
| 5,959,383 A | 9/1999 | Winzen et al. |
| 5,959,520 A | 9/1999 | Stelter et al. |
| 5,969,452 A | 10/1999 | Halsey et al. |
| 5,986,372 A | 11/1999 | Joffe |
| 6,022,349 A * | 2/2000 | McLeod et al. ............... 606/58 |
| 6,061,597 A * | 5/2000 | Rieman et al. ................ 607/51 |

* cited by examiner

MAGNETIC ARRAY IMPLANT AND METHOD OF TREATING ADJACENT BONE PORTIONS

FIELD OF THE INVENTION

The present invention relates to apparatus and methods for stabilizing and maintaining adjacent bone portions in predetermined desired relationships and constraining one, two or three-dimensional motion and/or rotation of the adjacent bone portions. More particularly, the present invention relates to a magnetic apparatus with at least two magnetic arrays, each of which may include at least one magnet arranged in a predetermined manner and each magnetic array generating a magnetic field therearound. Once implanted and secured to the adjacent bone portions, the magnetic apparatus provides interacting magnetic fields in the area of the bone portions and transduces magnetic energy into mechanical energy and mechanical energy into potential magnetic energy, thereby reproducing functionally anatomic and/or anatomically advantageous arrangement of the bone portions.

BACKGROUND OF THE INVENTION

Orthopedics is a medical subspecialty that treats disorders of the human body related to bones, muscles, ligaments, tendons, and joints, with its current emphasis on the treatment of the bones and joints. The treatment of bone and joint disorders can be generally subclassified into categories including the treatment of bone fractures, joint instability, early stage arthritis, and end stage arthritis. Originally, the treatment of orthopedic conditions had mainly relied on casting and bracing. However, with the advent of new implantable materials and development of better joint replacement prostheses, orthopedics shifted its focus to become increasingly more of a surgical subspecialty. With improved materials, better engineering, and a better understanding of the human body, the practice of orthopedic medicine and biomechanical experimentation have made remarkable progress. The treatment of bone fractures and joint disorders has continually been refined to the present state-of-the-art. The last 40 years have shown a myriad of innovations that have concentrated specifically on developing static mechanical design characteristics and new implantable materials used for fracture treatment and in total joint arthroplasties. These static mechanical design characteristics have been directed to solutions for problems concerning wear, stability, and methods of fixation for the total joint arthroplasties. They have also been utilized to improve the current state of the art concerning fracture treatment.

There have been some attempts to develop applications that utilize nonmechanical forces to augment the treatment of particular orthopedic problems. For example, pulsating electromagnetic field has been used as an adjunct to stimulating bone healing. Biochemical and biomaterial means have been used to alter the milieu at fracture sites and in joints to aid healing and to decelerate disease processes. Others have attempted to utilize magnetic fields in treatment of bone and joint disorders as well. For example, U.S. Pat. No. 4,024,588 to Janssen, et al. describes artificial joints with magnets. U.S. Pat. No. 4,029,091 to Von Bezold et al. discloses a method of applying plates to fractured bones so as to allow limited motions of the bone fragments when subjected to an externally generated electromagnetic force. U.S. Pat. No. 4,322,037 to Esformes et al. suggests a elbow joint including mechanically interlocking joint components with the inclusion of a magnetic force on the joint. U.S. Pat. No. 5,595,563 to Moisdon discloses a method of repositioning body parts through magnetic induction generated by extracorporeal magnetic or electromagnetic devices. U.S. Pat. No. 5,879,386 to Jore describes an apparatus to hold bones apart which can also be adjustable from inside the joint, possibly through arthroscopic means. The disclosed devices and methods had only limited uses for specific orthopedic problems. However, these designs are generally not practically feasible due to errors or misconceptions related to the practical application of orthopedic surgical treatments or, more importantly, a lack of understanding concerning the properties of permanent magnets in relationship to the mechanical environment found in the human body, especially as they relate to the normal functions of bones and joints. Accordingly, there remains a need in the art for improved apparatus and methods for less invasively locating and restraining bones in treatment of orthopedic conditions.

SUMMARY OF THE INVENTION

The present invention generally relates to apparatus and methods for controlling forces at adjacent bone portions and/or constraining motion of the adjacent bone portions in one or more dimensions. More particularly, the present invention relates to a magnetic apparatus with at least two magnetic arrays each of which is constructed and implanted in a predetermined manner and generates interacting magnetic fields. Once implanted and secured to the adjacent bone portions, the apparatus provides interacting magnetic fields in the vicinity of the adjacent bone portions and is capable of transducing magnetic energy into mechanical energy and mechanical energy into potential magnetic energy, thereby reproducing functionally anatomic and or anatomically advantageous positions of the bone portions.

An apparatus for treating adjacent bone portions according to the invention includes first and second magnetic arrays. The first magnetic array is configured and dimensioned to be secured to a first adjacent bone portion and to provide a first magnetic field having first predetermined field characteristics and the second magnetic array is configured and dimensioned to be secured to a second adjacent bone portion and to provide a second magnetic field having second predetermined field characteristics. The first and second predetermined field characteristics are selected to interact such that the magnetic arrays cooperate to urge the adjacent bone portions into the predetermined desired relationship and constrain relative motion between the bone portions in at least two dimensions. Preferably, one or both magnetic array may comprise multiple magnets to provide a composite magnetic field, which may be symmetrical or asymmetrical. In one preferred embodiment, interaction between the first and second magnetic fields urges the arrays into a predetermined relationship with a defined reference point confined within a boundary defined by the magnetic field of one of the magnetic arrays.

According to a further aspect of the invention, the first predetermined field characteristics comprise magnetic equipotential surfaces or lines forming at least two first peaks defining a valley therebetween and the second predetermined field characteristics comprise magnetic equipotential surfaces or lines forming at least one second peak. Preferably, the peaks and valleys are three dimensional, for example at least two first peaks and valley therebetween being defined by a three dimensional, rotated sinusoid, and at least one second peak being defined by a three dimensional paraboloid. The first and second magnetic arrays are then positioned with respect to each other such that the second peak is received between the at least two first peaks. In other words, the field of one array preferably penetrates the field of the opposite array. In this embodiment the second peak is received within, e.g., the annulus of the toroid which may be topologically described as a cup-shaped region generated by rotating a sinusoid about its vertical axis. Alternatively, the first magnetic array is configured and dimensioned to provide the predetermined field characteristics with magnetic flux lines such that at least two peaks have different magnitudes.

In a further alternative embodiment, the apparatus according to the invention also comprises a first magnetic array and at least a second magnetic array. Further arrays may be provided. In this embodiment, the first array includes at least two magnets, configured and dimensioned to be secured to a first adjacent bone portion and to provide a first, composite magnetic field having first predetermined field characteristics such as magnetic flux lines defining at least one region of first magnetic intensity bounded by one or more regions of second magnetic intensity. The second magnetic array is configured and dimensioned to be secured to a second adjacent bone portion and to provide a second magnetic field having second predetermined field characteristics such as magnetic equipotential lines defining at least one region of third magnetic intensity. The regions of different magnetic intensity interact to urge the adjacent bone portions into the predetermined desired relationship and constrain relative motion between the bone portions in at least two dimensions. According to various alternatives, the regions of second and third magnetic intensity may have approximately the same magnetic intensity or the regions of second and third magnetic intensity may have different magnetic intensities and the regions of first and second magnetic intensity may have opposite polarities or the regions of first and second magnetic intensity may have the same polarity.

In a further alternative embodiment, the first and second magnetic arrays are secured to the adjacent bone portions at a predetermined distance apart along a first axis, and are oriented with respect to each other in a predetermined relationship along at least a second axis orthogonal to the first axis. The second magnetic array includes at least one magnet. At least two magnets of the first array and at least one magnet of the second array are arranged with common poles in opposition to produce a predetermined repulsive force therebetween at the predetermined distance. Relative movement between the arrays along the second axis away from the predetermined relationship is resisted by interaction between the magnetic fields in the regions of second and third intensity.

In a further aspect of the invention, each array has an opposing face and a back face, and comprises at least two magnets, each magnet having a polar axis. The magnets of each array are aligned with their polar axes substantially parallel such that the poles of each magnet are adjacent and disposed at the faces of each array. The arrays thus may be adapted to be secured to adjacent bone portions opposite to each other with the opposing faces facing together and in a predetermined positions with respect to each other along a first axis substantially parallel to the polar axes and along at least a second axis substantially orthogonal to the polar axes. In one alternative embodiment, the magnets of each array are aligned with opposite poles positioned on the opposing faces and the predetermined position along the first axis comprises the first and second array being at least substantially in contact along the opposing faces. In this embodiment, interaction between the magnetic fields resists relative rotation between the arrays. In another alternative, the magnets of each array are aligned with the same poles positioned on the opposing faces and the predetermined distance along the first axis comprises a predetermined spacing. In this alternative embodiment, interaction between the magnetic fields resists reduction of the predetermined spacing and resists movement away from the predetermined position along the second axis while permitting rotation thereabout or about other axes positioned adjacent to the second axis. Moreover, in this latter embodiment, at least one of the magnetic arrays may further comprise at least one magnet disposed in the array with an opposite pole positioned on the opposing face.

In a method for treating adjacent bone portions according to the invention, first and second magnetic arrays are secured to adjacent bone portions, each array being configured and dimensioned to provide a magnetic field having predetermined field characteristics. The arrays are positioned in a desired relationship. Relative motion of the adjacent bone portions is constrained in at least two dimensions, maintaining the desired relationship through interaction of the first and second magnetic fields. An alternative method according to the invention involves securing a first magnetic array to a first adjacent bone portion to provide a first composite magnetic field therearound, securing a second magnetic array to a second adjacent bone portion to provide a second composite magnetic field therearound, and disposing the first and second magnetic arrays in opposition to each other to simultaneously generate both repulsive and attractive force therebetween, thereby urging the adjacent bone portions into a predetermined desired relationship and constraining relative motion of the adjacent bone portions in at least two dimensions. In a further aspect of the invention, the first and second adjacent bone portions form opposing bone portions of an articular joint and wherein the magnetic fields interact to reduce the joint reactive forces while constraining the bone portions to move in a natural joint motion. In an alternative aspect of the invention, the first and second adjacent bone portions are opposite sides of a bone fracture and the magnetic fields interact to reduce and stabilize the fracture fragments.

According to further aspects of the invention, a magnetic array may be constructed by arranging one or more magnets or arranging the poles of the magnets (both collectively referred to as "magnets" hereinafter) in a predetermined configuration and/or orientation. Due to the coincidence of the magnetic fields of individual adjacent magnets, the magnetic array creates a composite magnetic field which is capable of exerting two- or three-dimensional magnetic force upon objects disposed nearby. By manipulating properties, shapes, and other characteristics of each magnet and by arranging them in a predetermined configuration and/or orientation, the magnetic arrays and their interaction can be utilized to control forces between the adjacent objects and/or constrain their motion in two or three dimensions including rotation.

In another aspect of the invention, the magnets of the magnetic array may be secured into a housing, while maintaining the configuration and/or orientation thereof. By providing prearranged configuration and/or orientation thereto, the magnetic array can be readily adapted to treat variety of orthopedic conditions. This arrangement avoids potentially unpredictable implantation of individual magnets into different locations in the adjacent bone portions, simplifies the implantation procedure, reduces the time of the surgical procedure, minimizes complications following the surgery, facilitates the healing process, and provides a treatment option that is easier to perform and can be performed in a competent fashion by a greater number of surgeons.

In yet another aspect of the invention, the magnetic arrays are implanted into adjacent bone portions so as to control forces at the adjacent bone portions and/or to constrain the motion of adjacent bone portions in one or more dimensions. When one magnetic array is disposed in an opposed relationship to another magnetic array, the composite magnetic fields of each of the magnetic arrays interact with each other, and generate dynamically interacting magnetic fields between and/or around those magnetic arrays. Characteristics of the interacting magnetic fields can be specifically controlled by manipulating properties, shapes, and/or other characteristics of each individual magnet in each magnetic array, because the resultant of the interacting magnetic fields is a vector sum of the individual composite magnetic fields of each magnetic array. By manipulating the repulsive and/or attractive forces generated therebetween, the magnetic arrays can provide potential energy to do work along the axis parallel and orthogonal to the direction of the magnetic polarity, as well as provide rotational stability for particular array designs to the adjacent bone portions. This potential energy can be used to reduce the reactive force between the bone portions, and/or limit motion between the bone portions. According to the invention, the orthopedic magnetic apparatus including the foregoing magnetic arrays may be applied to various orthopedic conditions such as long bone fractures, carpal bone fractures, joint instability, early arthritis and end stage arthritis. They may also be used to augment the designs of other total joint components. In treating fractures, the magnetic arrays of the invention may be arranged to create dominant attractive force, thereby providing the structural and/or rotational stability thereto.

As indicated, in one aspect of orthopedic application of the present invention, the magnetic arrays described herein above may be applied to treat degenerative conditions such as arthritis. For such degenerative conditions, the magnetic arrays may preferably be arranged to create dominant repulsive force, thereby providing potential magnetic energy to counteract mechanical forces along the axis parallel to composite magnetic force vector and provide stability along the axis orthogonal to the composite magnetic force vector. Benefits may be realized in reducing mechanical contact between the intact cartilage of the bone portions at a joint by reducing the joint reactive force and providing the additional means of control to diminish joint instability and/or the progression of joint disease. Moreover, the invention may be employed in or with prostheses to reduce the mechanical contact and the damage caused by friction between implanted prosthetic components, reducing joint reactive force, and providing the stabilizing capability, thereby decreasing pain associated with the end-stage arthritis and/or extending the functional life of the implanted components.

The term "adjacent bone portions" generally refers to any bones or portions thereof which are disposed adjacent to each other. The "adjacent bone portions" or simply the "bone portions" may mean any bones or their portions positioned adjacent to each other, whether they are separate or functionally coupled with each other, and/or mechanically contacting each other due to anatomical reasons, non anatomic reasons and/or surgical treatments. For example, a tibia and fibula, a radius and ulna, and a femur, tibia, and fibula are a few representative pairs or groups of the bones anatomically disposed adjacent to each other; a femur and tibia, a humerus and ulna, and a humerus and scapula are exemplary bone pairs functionally coupled to each other through a knee joint, elbow joint, and shoulder joint, respectively; and a clavicle and sternum are the bones mechanically contacting each other. The "adjacent bone portions" may also include any two or more bone segments which are to be positioned adjacent to each other, and/or contacting each other. Examples of such bones may include any number of fractured segments of a bone(s) and/or joint(s).

The terms "equi-potential line" and "equi-potential surface" mean, respectively, any curvilinear two-dimensional line and three-dimensional surface, representing characteristics of a magnetic field generated around a magnet(s). The "equipotential surface" is perpendicular to magnetic fluxes emanating from the magnet and is drawn by connecting points of the same magnetic intensity on the magnetic fluxes. The "equipotential line" is obtained by taking a cross-section of the "equipotential surface" in a predetermined direction. Thus, the "equipotential line" is a subset of "equipotential surface" and also perpendicular to the magnetic fluxes in the predetermined direction. For ease of illustration and simplicity, both "equipotential line" and "equipotential surface" will be collectively referred to as "equipotential line" hereinafter. Accordingly, "peaks," "valleys," and "gaps" of the "equipotential lines" are inclusive of those depicted in the two-dimensional "equipotential lines" as well as those in the three-dimensional "equipotential surfaces."

DETAILED DESCRIPTION OF THE INVENTION

The following description provides exemplary embodiments of orthopedic methods and apparatus according to the present invention. In particular, the description provides examples of magnetic arrays, orthopedic apparatus incorporating those magnetic arrays, and applications of such magnetic arrays and orthopedic apparatus to various orthopedic conditions such as fractures, joint instability, early stage arthritis, end stage arthritis and augmentation of total joint components. This list and the examples contained herein are merely illustrative, and not exhaustive.

Figure 1A:
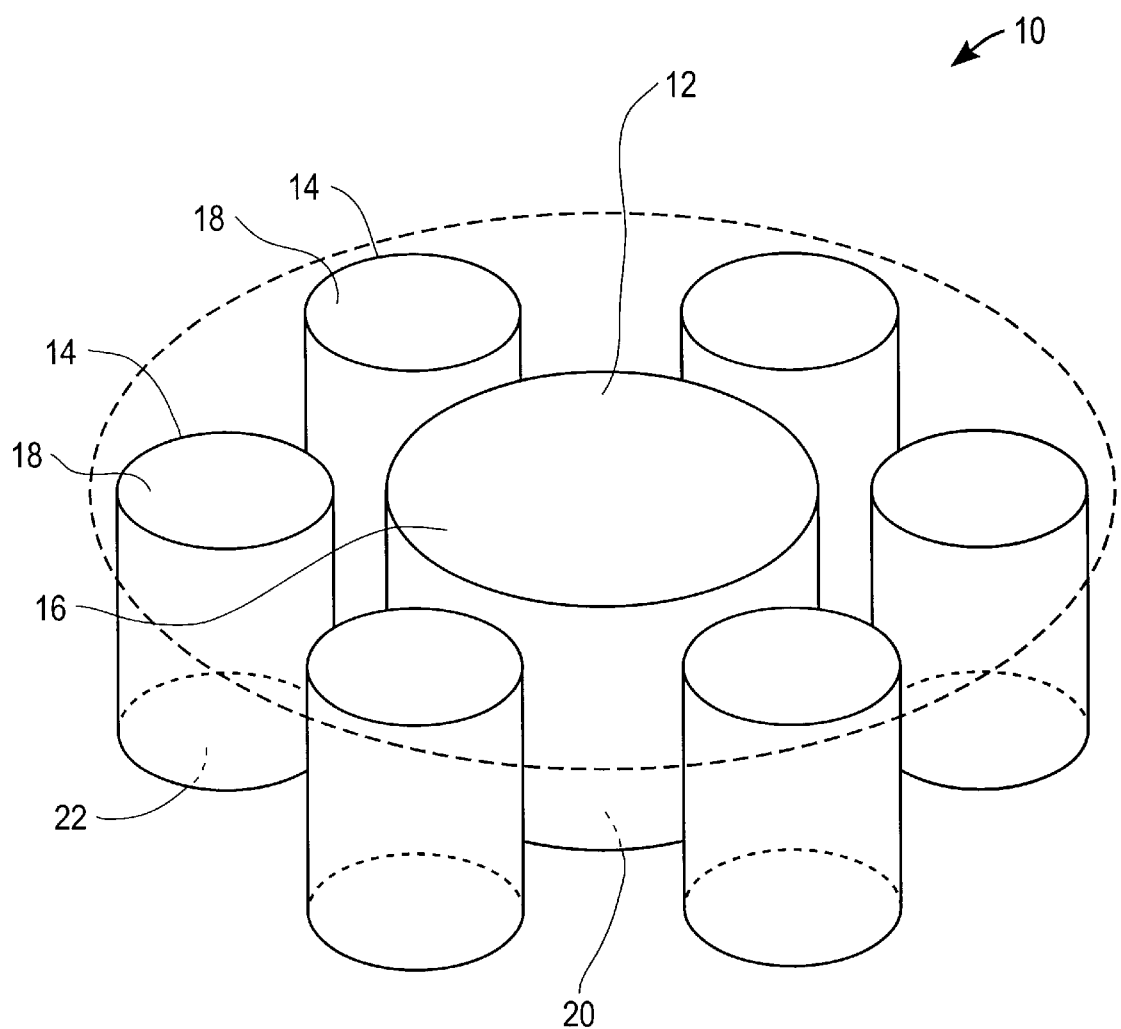
FIG. 1A is a perspective view of an example of a magnetic array with multiple magnets according to the present invention.
Figure 1B:
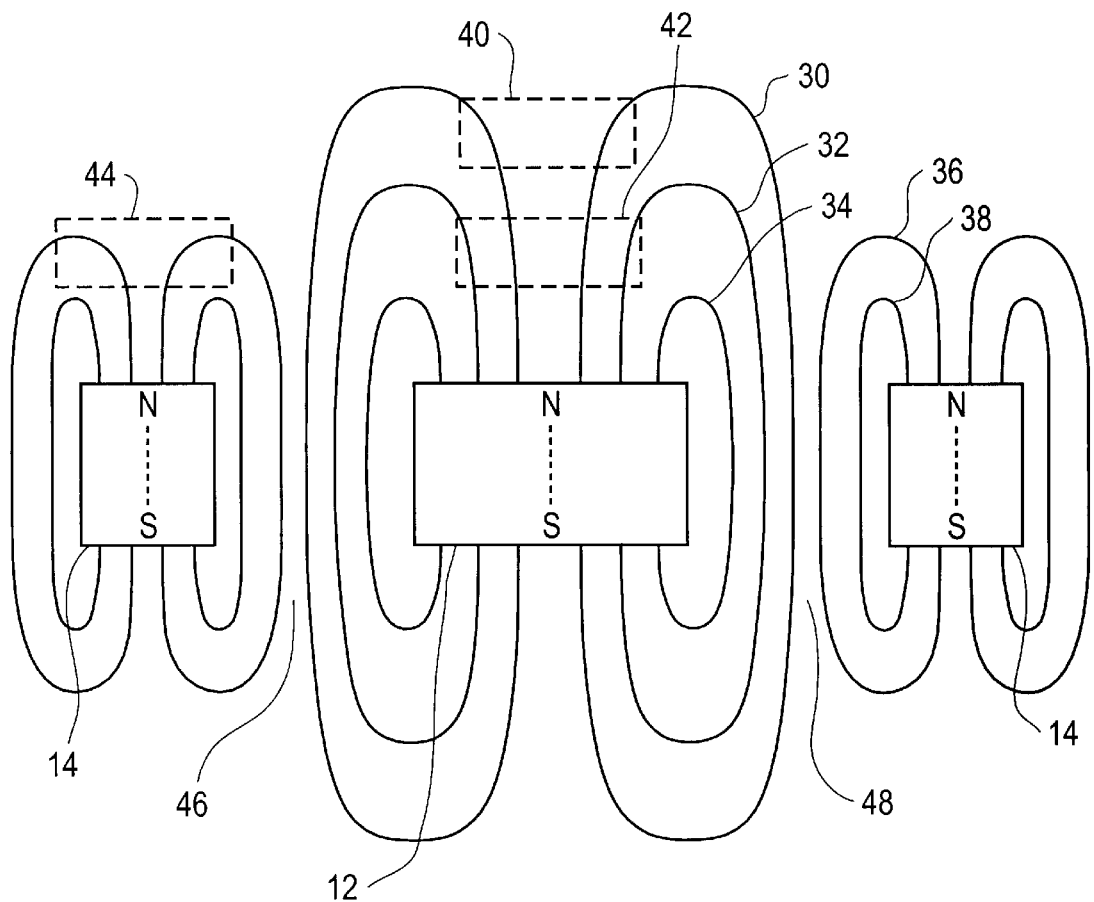
FIG. 1B is a cross-sectional schematic view of magnetic flux lines of a composite magnetic field generated-around the magnetic array of FIG. 1A according to the present invention.
Figure 1C:
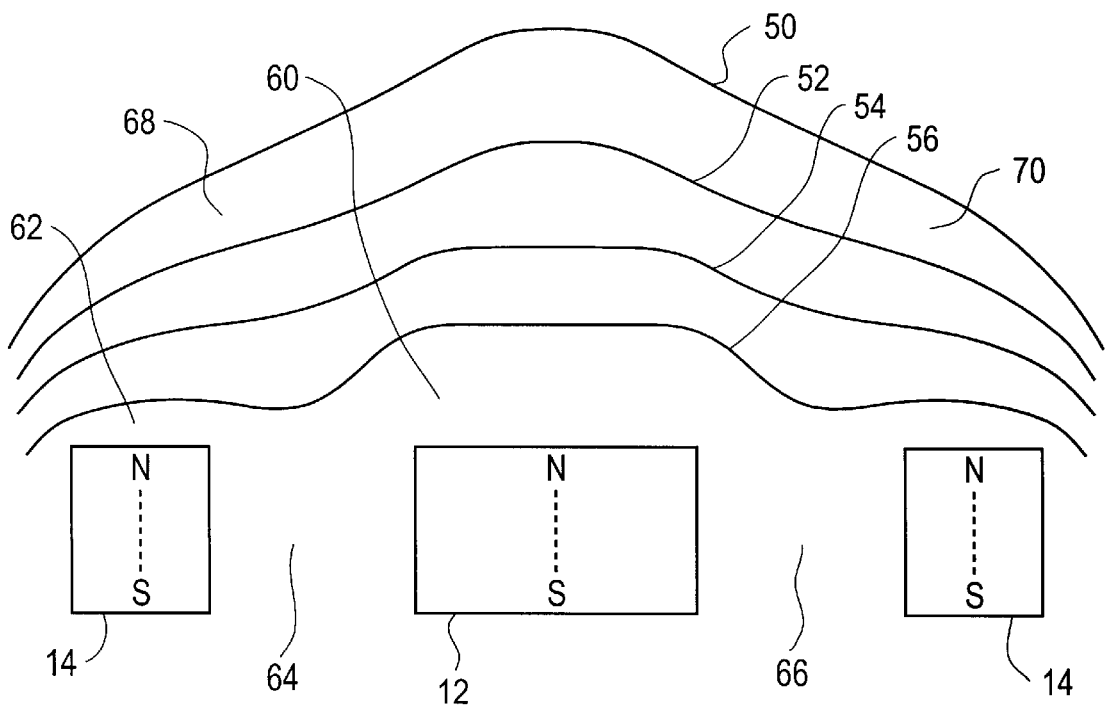
FIG. 1C is a cross-sectional schematic view of equipotential lines of a composite magnetic field generated around the magnetic array of FIG. 1A according to the present invention.

In one aspect of the invention, a magnetic array is provided by arranging one or more magnets in a specific configuration adapted to the particular application. FIGS. 1A, 1D, 1G, and 1I illustrate various embodiments of such magnets and magnetic arrays, while FIGS. 1B, 1C, 1E, 1F, and 1H illustrate characteristics of composite magnetic fields created by those magnetic arrays and their interactions. As shown in FIG. 1A, magnetic array 10 includes center magnet 12, which may be cylindrical, positioned at a center of a group of six peripheral magnets 14. In this embodiment all magnets 12, 14 are arranged with their north poles at their top faces 16, 18 and the south poles at their bottom faces 20, 22. The center magnet 12 may be selected to have greater "magnetic flux density" than the peripheral magnets 14 as schematically illustrated in FIGS. 1B and 1C. Note that references to orientation used herein, such as "top" and "bottom" or "above" and "below", are used only for clarity in discussing the figures and are not limiting of the invention described, which may be used in any orientation according to the teachings herein.

In alternative embodiments, different characteristics of the magnet design may be altered to provide the center magnet 12 with greater or lesser magnetic flux density. When all of the magnets in the array are made of the same material, their magnetic flux density can be increased by altering the placement, height, thickness or surface area of the magnet. Thus, center magnet 12 may differ from peripheral magnets 14 accordingly. Alternatively, center magnet 12 may be made of a different magnetic-energy material with a higher $(BH)^{max}$ such as any one of a range of NdFeB materials or any other magnetic material with appropriate flux density for the particular use, while peripheral magnets 14 are made of lower $(BH)^{max}$ material. Such a center magnet may be the same size or smaller than peripheral magnets 14. Regardless of the size or material, center magnet 12 may be fixed in the array at a level higher (or lower) with respect to the present surface than that of peripheral magnets 14. By positioning center magnet 12 at a higher (or lower) position relative to the other magnets in the array, the center magnet will contribute more (or less) to the composite magnetic field, affecting the object placed above (or below) magnetic array 10 to a greater or lesser extent.

FIG. 1B is a cross-sectional schematic view of magnetic flux lines of a composite magnetic field generated by the magnetic array of FIG. 1A according to the present invention. In FIG. 1B, magnetic flux lines 30, 32, 34 emanate from center magnet 12, whereas magnetic flux lines 36, 38 emanate from peripheral magnet 14. Because the magnetic axes (dotted lines drawn inside magnets to connect their opposite poles) of magnets 12, 14 are parallel to each other, the magnetic fields created by peripheral magnets 14 are generally parallel to the longitudinal axis of center magnet 12.

The magnetic flux lines may also be used to assess a spatial distribution pattern of magnetic intensity of the composite magnetic field of the magnetic array 10. For example, the magnetic intensity can be assessed in terms of "magnetic flux" which is defined as the amount of magnetic flux lines crossing a given area (such as those denoted by numerals 40, 42, 44). Alternatively, the magnetic flux may be calculated as an integral of a component of magnetic flux density perpendicular to the area divided by the area. Comparison of the magnetic flux densities crossing the areas 40 and 42 reveals that the magnetic intensity or magnetic flux decreases as the distance between magnet 12 and areas 40, 42 increases. In addition, magnetic flux lines 30–34 emanating from stronger center magnet 12 extend farther into the medium than flux lines 36, 38 emanating from weaker peripheral magnets 14. Because the same poles of the center and peripheral magnets are disposed on the same side of magnetic array 10, the center and peripheral magnets generate repulsive force acting against each other. Presence of such repulsive force is represented by annular zones 46, 48 formed between center and peripheral magnets 12, 14. It is appreciated that magnetic flux lines 30, 36 which emanate from different adjacent magnets but run in the same direction also delineate the existence of such repulsive force.

The spatial distribution pattern of the magnetic intensity (or flux) can also be assessed by mapping equipotential lines of force for the composite magnetic field. FIG. 1C is a cross-sectional schematic view of equipotential lines of the composite magnetic field generated around the magnetic array of FIG. 1A according to the present invention. Equipotential lines 50, 52, 54, 56 are curvilinear lines representing a vector sum of individual magnetic fields generated by center and peripheral magnets 12, 14. The equipotential lines are perpendicular to corresponding magnetic flux lines of the individual magnets 12, 14, and are drawn by connecting points of the same magnetic intensity on the magnetic flux lines. As illustrated in the FIG. 1C, the mapping of equipotential lines 50–56 facilitates the analysis of composite magnetic fields as well as provides a graphic representation of the characteristics of the composite magnetic fields. The map of equipotential lines 50–56 demonstrates that the contour of the equipotential lines depends not only on the specific characteristics of the magnets (i.e., material composition, size, shape, cross-sectional area, position, and orientation) but also on the distance from the magnet(s). FIG. 1C illustrates exemplary effects of distance on the contour of the equipotential lines. In the regions 60, 62, proximate to magnets 12 and 14, intensity (or flux) of the composite magnetic field is predominantly determined by that of the nearest magnet. Therefore, the contour of equipotential lines 54, 56 approximates the contour of the surface of the nearest magnet, which is manifest by the relatively flat profile of equipotential lines 54, 56 on or above magnets 12, 14. Transition zones are formed in gaps 64, 66 between magnets 12, 14 wherein equipotential lines 54,56 form curves, the extent of which is generally proportional to the difference in the magnetic strengths between the neighboring magnets. In regions 68, 70, far away from magnets 12, 14, the intensity of the composite magnetic field generally decreases in proportion to a square of the distance from the magnet face. More importantly, however, the contour of equipotential lines 50, 52 becomes less dependent on the surface contour of the magnets. Rather, equipotential lines 50, 52 become smoother due to the summation of the weak magnetic fields of individual magnets 12 and 14.

Figure 1D:
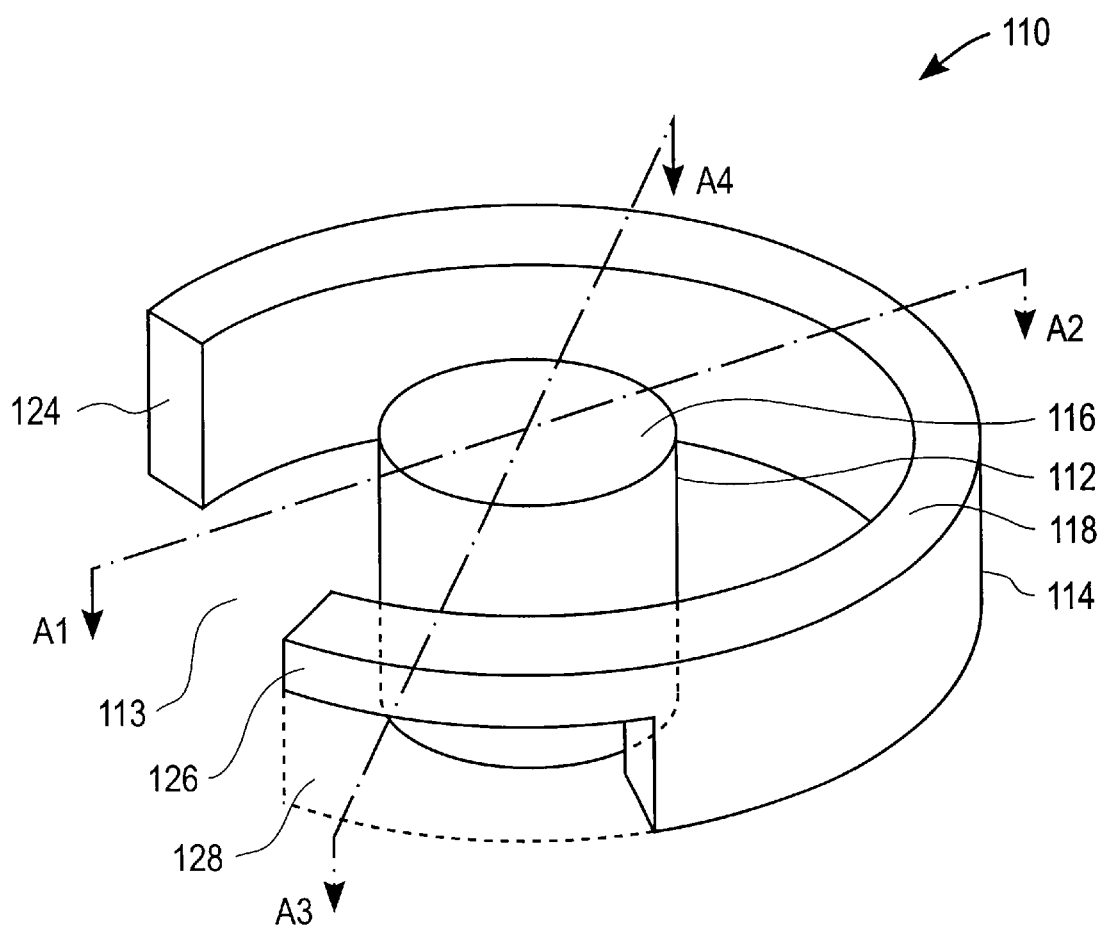
FIG. 1D is a perspective view of an alternative example of a magnetic array with multiple magnets arranged according to the present invention.

FIG. 1D is a perspective view of another embodiment of a magnetic array having multiple magnets arranged in a predetermined manner according to the present invention. Magnetic array 110 includes single C-shaped peripheral magnet 114 and cylindrical center magnet 112 disposed at a center of peripheral magnet 114. Peripheral magnet 114 is designed with a gap 113 between two ends 124, 126 so as to decrease the magnetic intensity therearound. The lower portion 128 beside gap 113 is also truncated to decrease the magnetic intensity there above. Alternatively, gap 113 and/or lower truncated portion 128 may be filled with a material having magnetic properties which differ from those of peripheral magnet 114. Both magnets 112 and 114 are arranged to have the north poles on their top faces 116, 118 and the south poles on their bottom faces 120, 122 (shown in FIGS. 1E and 1F). Accordingly, the magnetic axes and longitudinal axes of magnets 112 and 114 are generally parallel to each other. As described hereinabove, center magnet 112 is preferably designed to have greater magnetic flux density than peripheral magnet 114, e.g., by providing a larger center magnet 112, by making center magnet 112 of materials having greater magnetic energy, by positioning the center magnet at a level higher than that of the peripheral magnet or by configuring the center magnet to have a larger cross-sectional area. In many applications functional arrays are paired with one array having substantially the opposite configuration as the other array.

Figure 1E:
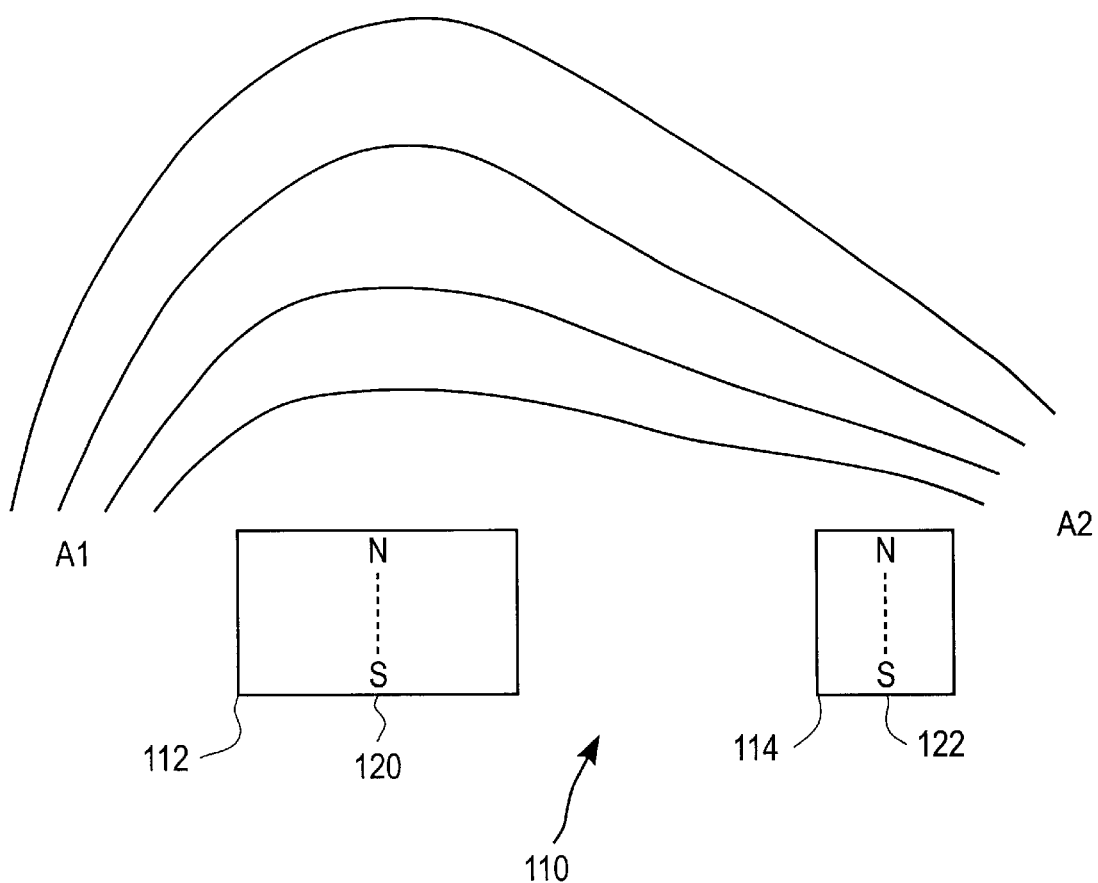
FIG. 1E is a cross-sectional schematic view of equipotential lines of a composite magnetic field through line A1–A2 of FIG. 1D according to the present invention.
Figure 1F:
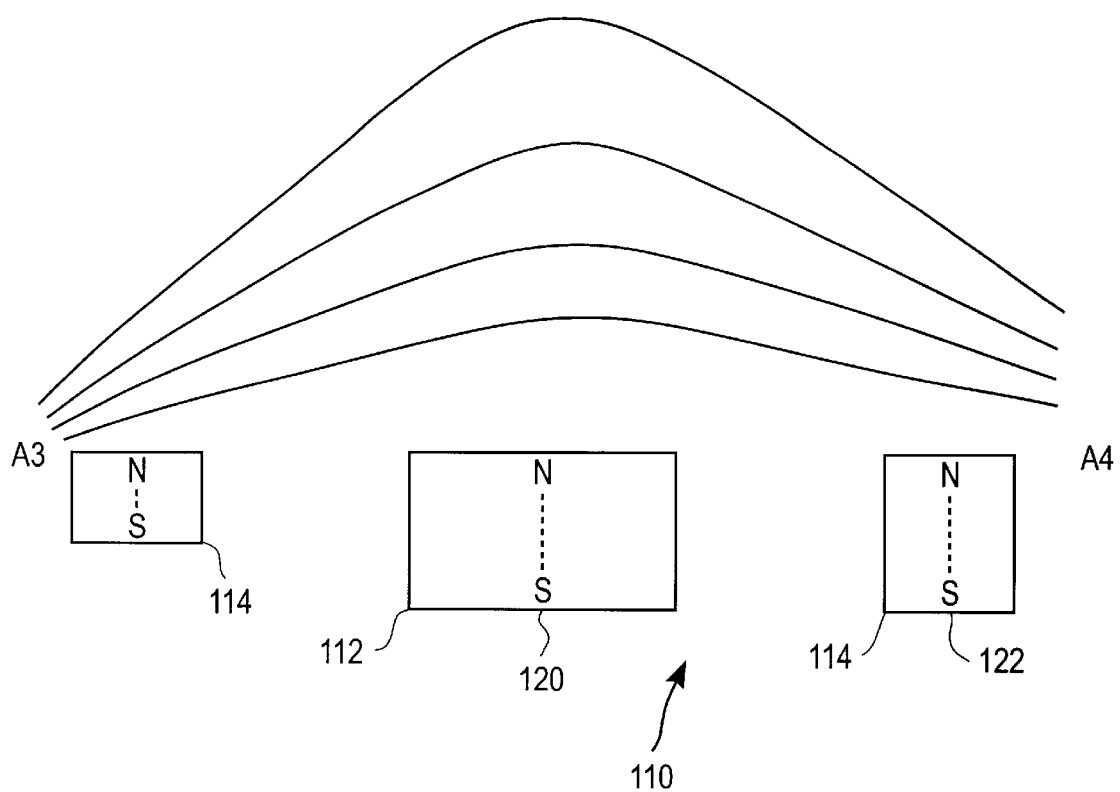
FIG. 1F is a cross-sectional schematic view of equipotential lines of a composite magnetic field through line A3–A4 of FIG. 1D according to the present invention.

FIG. 1E is a cross-sectional schematic view of equipotential lines of the composite magnetic field generated around the magnetic array of FIG. 1D according to the present invention, wherein the cross-section is taken through the array along the line A1–A2 of FIG. 1D. Because the line A1–A2 is drawn through gap 113 in the peripheral magnet 114, the magnetic field adjacent to gap 113 (or location A1) is substantially weaker than in the similar location on its opposite side (i.e., location A2). FIG. 1F is another cross-sectional schematic view of equipotential lines of the composite magnetic field generated around the magnetic array of FIG. 1D according to the present invention, wherein the cross-section is taken through the array along the line A3–A4 of FIG. 1D. Along the line A3–A4 drawn away from gap 113 of the peripheral magnet 114, the shapes of individual equipotential lines and the distribution pattern thereof are substantially similar to those of the magnetic array 100 described in FIGS. 1A to 1C, although the magnetic field above the truncated end 126 (or location A3) is weaker than its corresponding location on its opposite side (i.e., location A4). Accordingly, peripheral magnet 114 with the gap 113 and/or truncated portion 128 (or alternative material) generates an asymmetric magnetic field which in turn leads to create an asymmetric composite magnetic field for the entire array therearound. As will be discussed in greater detail below, this embodiment and others for asymmetric composite magnetic fields offer the benefit of constraining motion of above portion to a greater degree in one direction than another and at the same time allowing the comparative movement in one direction to be less constrained than in the other direction.

Figure 1G:
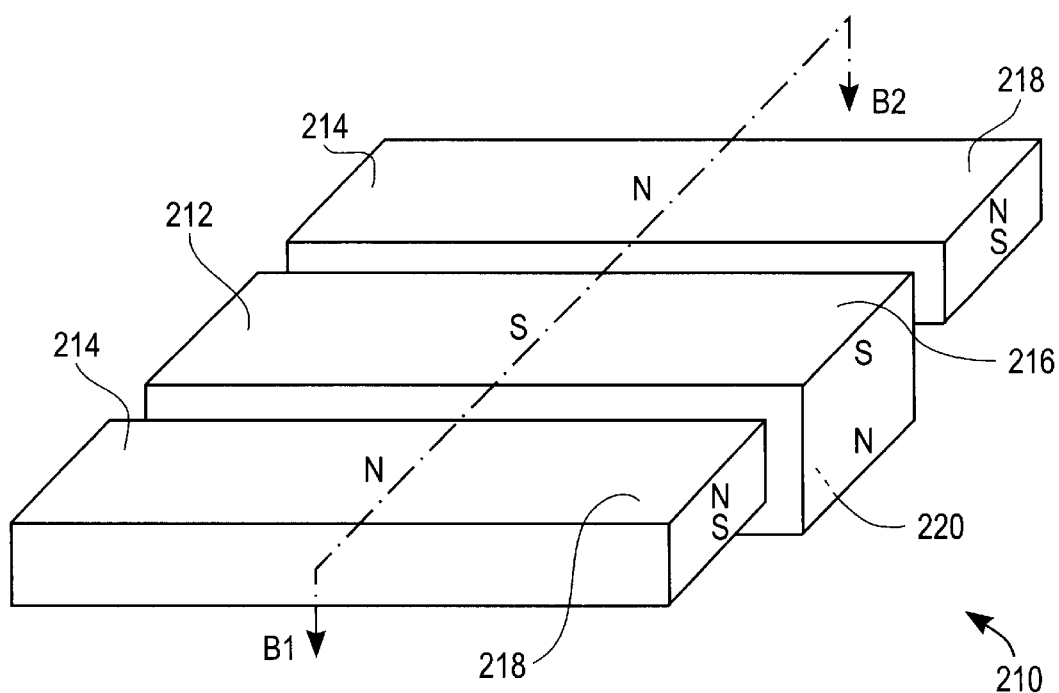
FIG. 1G is a perspective view of yet another magnetic array with multiple magnets arranged in a predetermined manner according to the present invention.

FIG. 1G is a perspective view of yet another magnetic array with multiple magnets arranged according to an alternative embodiment the present invention. Magnetic array 210 includes a rectangular center magnet 212 and two rectangular peripheral magnets 214 disposed on opposite sides of the center magnet 212. The south pole of center magnet 212 is positioned on top face 216 between the north poles of peripheral magnets 214. Similarly, the north pole of center magnet 212 is positioned on bottom face 220 between the south poles of peripheral magnets 214. Center magnet 212 may be arranged to have magnetic flux density greater than that of peripheral magnets 214, e.g., by making it thicker than peripheral magnet 214 as shown in the figure or by other methods described hereinabove. In addition, top faces 216, 218 of magnets 212, 214 are arranged to be flush with each other so as to provide magnetic array 210 with a flat upper surface.

Figure 1H:
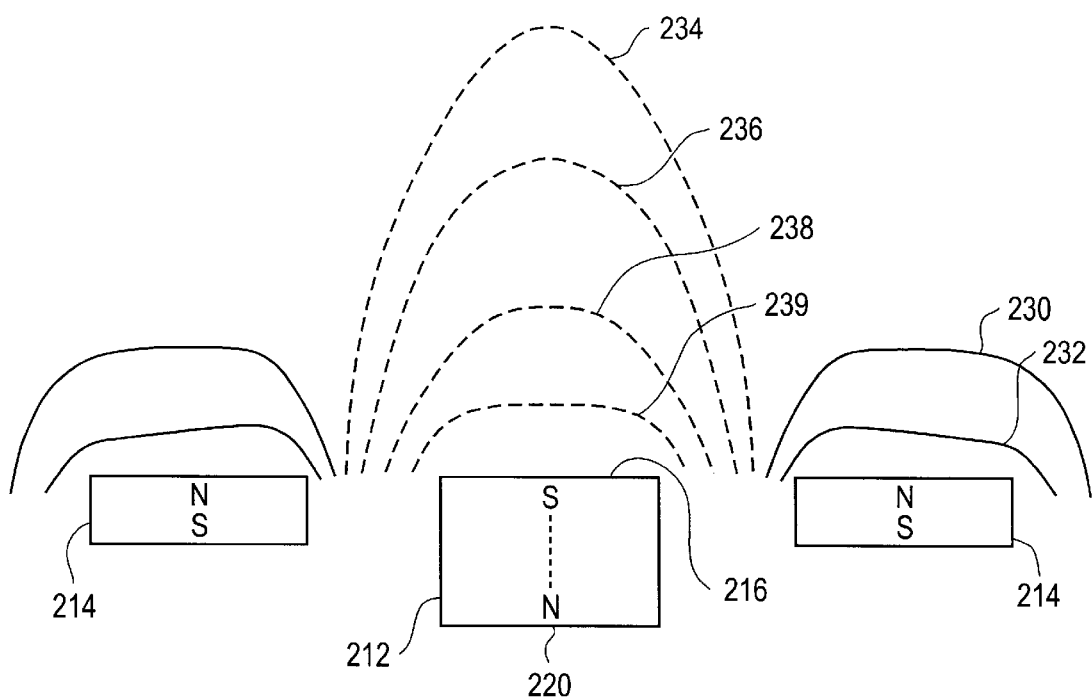
FIG. 1H is a cross-sectional schematic view of equipotential lines of a composite magnetic field through line B1–B2 of FIG. 1G according to the present invention.

FIG. 1H is a cross-sectional schematic view of equipotential lines of a composite magnetic field generated around the magnetic array of FIG. 1G according to the present invention, where the cross-section is taken along the line B1–B2 of FIG. 1G. Because the opposite poles are disposed adjacent to each other, presentation of the equipotential lines requires description of magnetic intensities having opposite polarities. Accordingly, solid lines 230, 232 are used to denote equipotential lines of magnetic fluxes emanating from the north poles of peripheral magnets 214, whereas broken lines 234, 236, 238, 239 are those emanating from the south pole of center magnet 212.

Figure 1I:
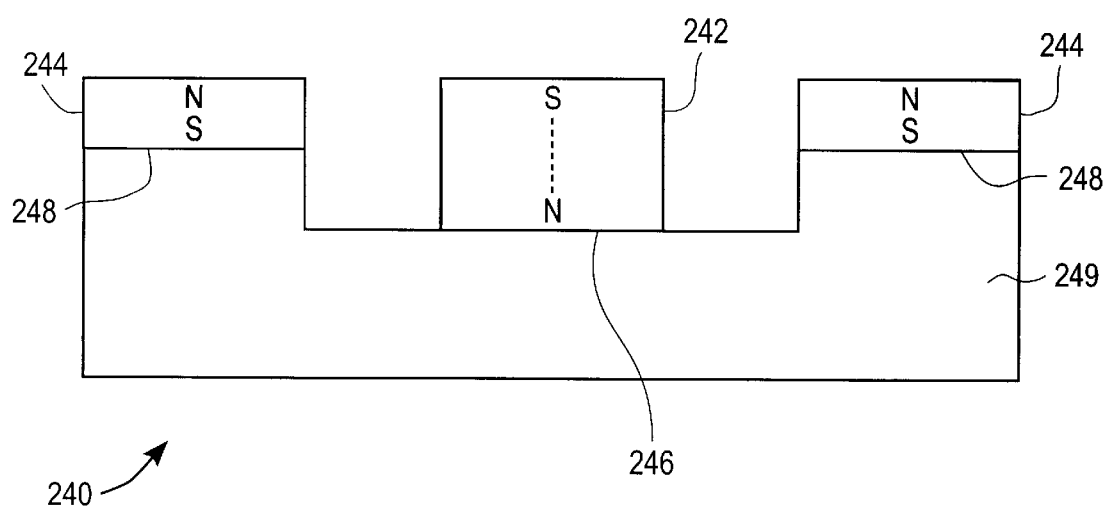
FIG. 1I is a cross-sectional schematic view of another alternative example of a magnetic array having a pole piece structure according to the present invention.

In general, magnetic arrays according to the invention are made of permanent magnets. Examples of such permanent magnets preferably include, but not limited to, rare earth cobalt magnets (e.g., samarium-cobalt, SmCo), and rare earth iron boron magnets (e.g., sintered neodymium-iron-boron, NdFeB). Magnetic arrays according to the invention may further include diamagnetic, paramagnetic, ferromagnetic, anti-ferromagnetic, and/or ferrimagnetic material, and/or any other materials that may be incorporated to affect or vary the configuration of the composite magnetic field created around the magnetic arrays. One example of such magnetic arrays is a pole piece where ferromagnetic material is placed at the north and/or south pole of one or more magnets so as to customize the magnetic field created around the magnetic array. Steel or other ferromagnetic material may be used to complete a circuit by contacting the magnets on their back surfaces. FIG. 1I is a cross-sectional schematic view of another alternative example of a magnetic array having a pole piece structure according to the present invention. Magnetic array 240 includes a center magnet 242 and peripheral magnets 244, wherein bottom faces 246, 248 of center and peripheral magnets 242, 244 are coupled to a ferromagnetic base 249. The center magnet may be cylindrical, positioned at a center of a group of peripheral magnets or inside a ring- or C-shaped peripheral magnet. Alternatively, the center and peripheral magnets may be rectangular, similar to those of FIGS. 1G and 1H. It is further appreciated that materials for the magnetic arrays may preferably have sufficient mechanical strength to survive the rigors and stresses of implantation and throughout the course of the orthopedic treatment.

It is appreciated that various factors may affect the contour of the equipotential lines. Examples of such factors may include, but not limited to, material, shape, size, polarity, magnetic strength, orientation, surface area and distribution pattern of the magnets. Further examples may also include embodiments where there are alterations in the orientation of the magnetic axis, the number and distribution pattern of poles on each side of the magnets, the presence of insulating or conductive material around or between the magnets, and the presence of symmetry or asymmetry of the magnets or magnetic arrays.

Figure 2A:
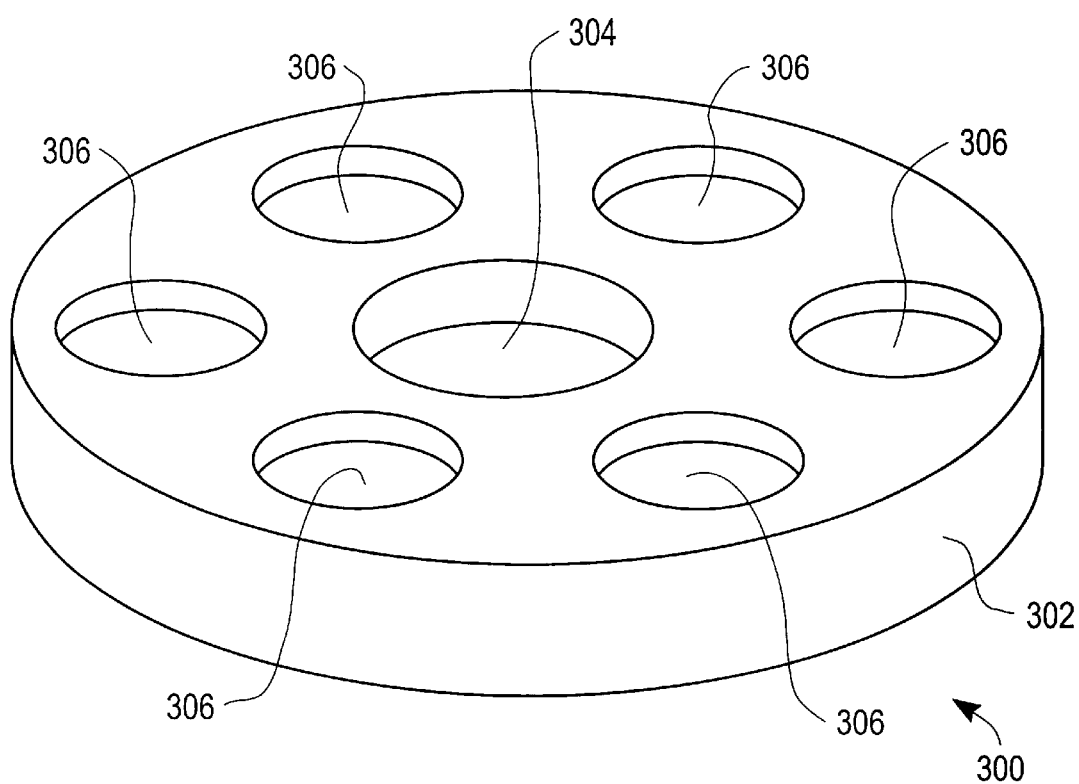
FIG. 2A is a perspective view of one embodiment of a housing for securing magnets of a magnetic array according to the present invention.
Figure 2B:
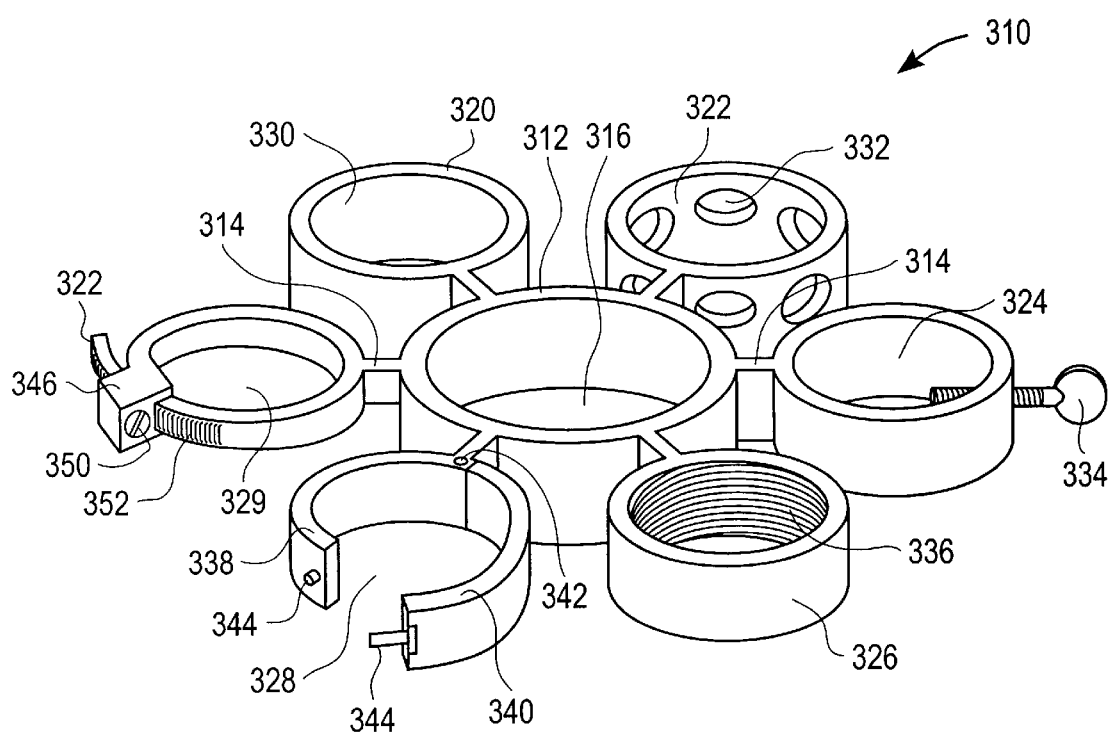
FIG. 2B is a perspective view of an alternate embodiment of a housing for securing magnets of a magnetic array according to the present invention.

In another aspect of the invention, the magnetic arrays may include a housing to support and secure the magnets of the array. Due to attractive or repulsive forces exerted by the magnets, the configuration of an unsecured magnetic array may deviate or be deformed from its predetermined arrangements as an individual unit. Accordingly, a housing may be shaped and sized to maintain the overall configuration or arrangement of the magnets and the orientation of each magnet with respect to the other ones. FIGS. 2A and 2B illustrate two exemplary embodiments for housings for the magnetic arrays.

FIG. 2A is a perspective view of a housing for securing magnets of the magnetic array of FIG. 1A according to an embodiment of the present invention. Housing 300 includes housing body 302 made of biocompatible or implantable polymers and/or other materials which will be described in greater detail below. Housing 300 also includes center receptacle 304 and multiple peripheral receptacles 306 disposed around center receptacle 304. Each receptacle forms a cavity shaped and sized to receive corresponding magnets. For example, receptacles 304, 306 may be arranged to have cavity diameters substantially equal to or slightly greater than the diameters of magnets 12, 14 of FIG. 1A, respectively. Each receptacle 304, 306 may be designed with a predetermined cavity depth such that only a predetermined portion or faces of magnets 12, 14 may be exposed after the assembly. Assembled magnets 12, 14 can be secured to housing body 302 by adhesives, a friction fit, an interference fit, threads, couplers, and/or other conventional coupling devices and methods known in the art.

It is appreciated that the shape and size of the receptacles do not have to conform precisely to those of the magnets. For example, receptacles may be arranged to receive magnets with different shapes and/or sizes by using, e.g., fillers, spacers, and/or other adaptors and couplers known in the art. Receptacles or magnets may also be designed to include additional size-independent coupling mechanisms known in the art, e.g., screws and latches. In addition, receptacles may be arranged to have standardized shape, size, and/or patterns. This embodiment offers a user the ability to customize the distribution pattern of the magnets of the magnetic array. Furthermore, magnets or receptacles may have adjustable insertion depth.

FIG. 2B is a perspective view of another housing for securing the magnets of the magnetic array of FIG. 1A according to the present invention. Housing 310 typically includes circular housing body 312 and multiple arms 314 disposed therearound. Housing body 312 defines center receptacle 316 arranged to receive a center magnet through its center cavity and to secure it thereto by a friction or interference fit. Multiple arms 314 extend from housing body 312 and include distal ends each of which terminates in at least one of multiple peripheral receptacles 320, 322, 324, 326, 328, 329. For example, first peripheral receptacle 320 receives a peripheral magnet through its cavity and secures the peripheral magnet thereto by a tapered inner wall 330. Second peripheral receptacle 322 also receives a peripheral magnet through its cavity but secures the peripheral magnet by auxiliary magnets (not shown) disposed in apertures 332 formed along a side wall of receptacle 322. Third peripheral receptacle 324 is arranged similarly to first receptacle 320, but secures a peripheral magnet thereto by a threaded hole and an interference screw 334 inserted therethrough. Fourth peripheral receptacle 326 includes threaded cavity wall 336 which receives a peripheral magnet having a threaded outer wall. Fifth peripheral receptacle 328 has stationary arm 338, movable arm 340 which is coupled to the receptacle 328 by a hinge 342, and latch 344 arranged to secure a peripheral magnet. Sixth peripheral receptacle 329 is provided with fastener 346 having screw 350 and threaded strip 352 engaged with screw 350. By rotating screw 350, threaded strip 352 may be fastened to secure a peripheral magnet therein. Other conventional securing mechanisms known in the art may also be used to secure peripheral magnets into housing 310.

The housing may be made of any conventional or hereafter conceived biocompatible or implantable materials. Examples of such materials may include, but not limited to, any biomedical grade polymers, non-corrosive metals, plastics and ceramics. It is appreciated that any non-biocompatible and corrosive materials may also be used to construct the housing as long as they are coated with a layer of or encased in a biocompatible or implantable material having an appropriate thickness. It is further appreciated that materials for the housing preferably have mechanical strength to survive the rigors and stresses of implantation and for the duration of the orthopedic treatment. The housing or at least a portion thereof may include magnetic, diamagnetic, paramagnetic, ferromagnetic, anti-ferromagnetic, and/or ferrimagnetic material, and/or any other materials that may affect or vary the configuration of the composite magnetic field created around the magnetic array. This embodiment offers the ability to custom design a magnetic array that generates the desired complex composite magnetic field therearound. The housing may also include a magnetic insulator or conductor disposed at appropriate locations. In particular, when the opposite poles of the magnets are disposed adjacent to each other, the insulator is provided between such magnets to minimize leakage of the magnetic field and unwanted interaction between those magnets. It is preferred that the magnet array be further coated with, incased by, embedded in or molded in biocompatible material for safety and ease of application. According to a further alternative embodiment described in greater detail below, the housing may comprise the components of a traditional implant.

In operation, magnets are provided to have suitable shape, size, polarity, and magnetic intensity. These magnets are positioned in the receptacles of the housing body according to predetermined distribution pattern, polarity, and orientation. Depending on the detailed configuration of the receptacles and distribution pattern thereof, a user may be allowed to customize the distribution pattern of the magnets, the orientation of each magnet with respect to the others, and the insertion depth of each magnet. Once the magnets are properly positioned on the housing, the magnets are secured to the housing by various conventional methods described hereinabove.

In another aspect of the invention, two or more magnetic arrays may be secured to the adjacent bone portions so as to stabilize the bone portions in a predetermined desired relationship and/or to constrain motion of the bone portions with respect to each other. If appropriate, the bone portions may be urged into proper relationship by the magnetic arrays. When one magnetic array is disposed adjacent to another magnetic array, composite magnetic fields of those magnetic arrays interact with each other, and generate a dynamic, interacting magnetic fields between or around the magnetic arrays. It is noted, however, that the characteristics of the interacting magnetic fields are determined by those of individual composite magnetic fields of each array and resultant force is obtained as a vector sum of the individual composite magnetic fields. FIGS. 3A to 3F illustrate exemplary embodiments of applications of such interacting magnetic fields.

Figure 3A:
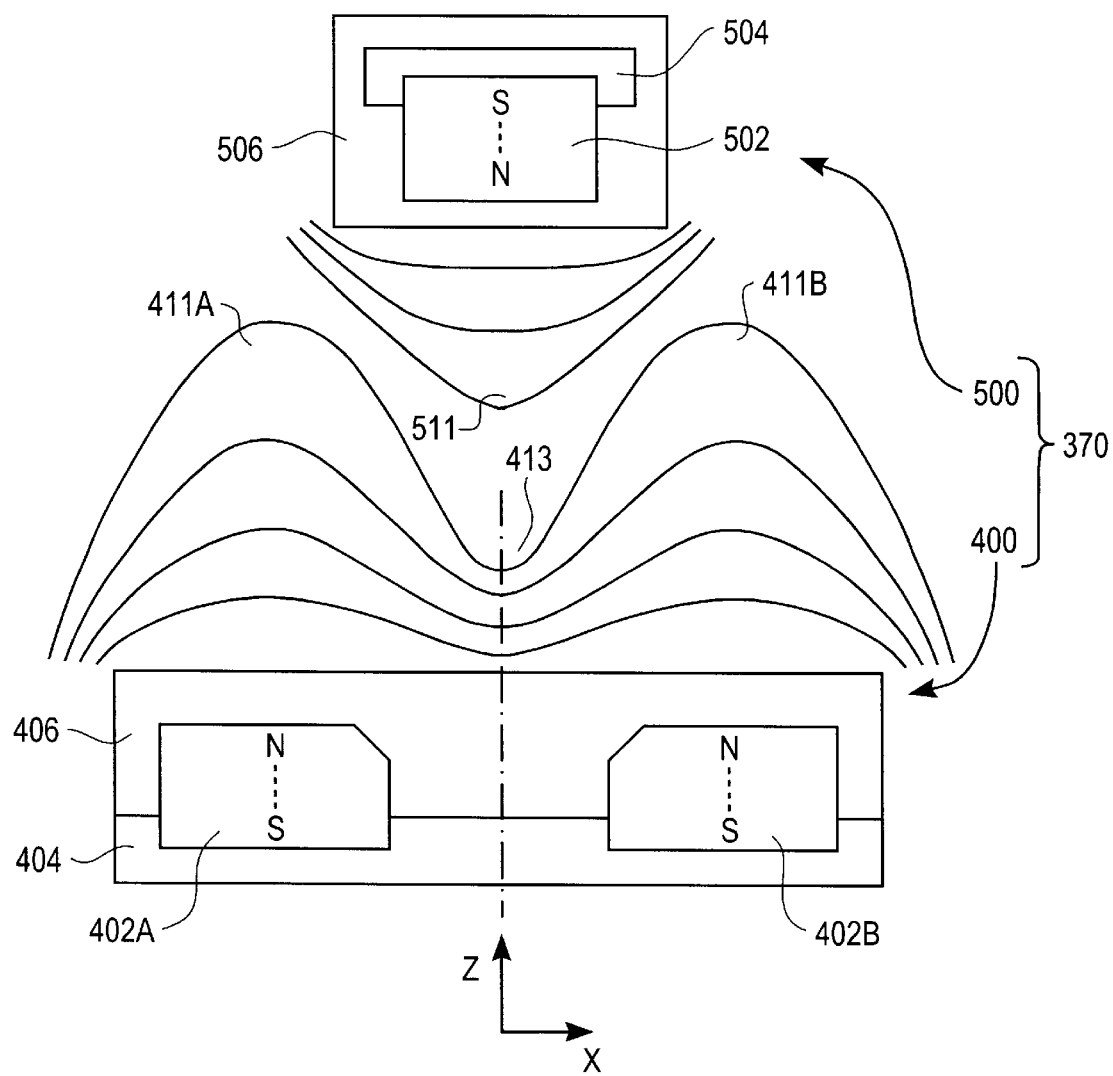
FIG. 3A is a cross-sectional schematic view of one embodiment of a magnetic apparatus for providing stabilizing magnetic field according to the present invention.

FIG. 3A is a cross-sectional schematic view of magnetic apparatus for providing stabilizing magnetic field according to the present invention. Exemplary magnetic apparatus 370 includes two magnetic arrays disposed adjacent to each other, i.e., first magnetic array 400 and second magnetic array 500 disposed opposite first magnetic array 400. First magnetic array 400 includes two magnets 402A, 402B secured to housing 404, with their upper faces flush with each other and their north poles facing upward. (Alternatively, magnets 402A, 402B may represent different cross-sectional portions of a single peripheral ring- or c-shaped magnet.) First magnetic array 400 may further include a cover 406 sealingly placed over magnets 402A, 402B and housing 404, thereby enclosing both magnets 402A, 402B and housing 404 therein. Because the same poles of magnets 402A, 402B are disposed on the same side, first magnetic array 400 generates a composite magnetic field where its equipotential lines form (in cross-section) two symmetric peaks 411A, 411B and a valley 413 therebetween. In three dimensions the magnetic field will have a cup-like, continuous, rotated sinusoidal shape. Second magnetic array 500 includes magnet 502 positioned on housing 504, with the same (north) pole oriented towards the opposing array. Both magnet 502 and housing 504 are encased inside an outer housing 506. Second magnetic array 500 generates a composite magnetic field with equipotential lines forming a single three dimensional peak 511 above the center portion of magnet 502.

When second magnetic array 500 is positioned above and adjacent to first magnetic array 400, with its north pole facing the north poles of the magnets in array 400, the composite magnetic fields of magnetic arrays 400 and 500 form dynamic interacting magnetic fields, wherein a "repulsive force" exerted between the two arrays 400, 500. Both the magnitude and the direction of this net repulsive force depend on the position of each magnetic array with respect to the other.

The embodiment of FIG. 3A offers the benefit of providing magnetic potential energy to the magnetic apparatus 370, i.e., it has potential to do work to offset any force that would cause one magnetic array to contact or increase the reactive force between it and the other array. For example, when a load is applied to second magnetic array 500 vertically (along the z-axis), the second array will tend to move vertically toward first magnetic array 400. As the magnitude of the load increases, the distance between the magnetic arrays will decrease, however, the repulsive force will at the same time increase in strength accordingly($\sim 1/r^2$) such that the two arrays reach an equilibrium state (application of excessive force will cause the magnets to come in contact). When an axial load is removed or decreased, the potential energy of the interacting magnetic fields is converted back to the mechanical energy, repelling second magnetic array 500 away from first magnetic array 400 to a new equilibrium position. As will be discussed in greater detail below, designs according to the invention, such as magnetic apparatus 370, beneficially minimize frictional damage or destruction of the adjacent bone portions of joints.

Furthermore, apparatus according to the invention may be designed to deter radial displacement of one magnetic array away from its centralized equilibrium position with the opposite array. Arrangement of the magnetic arrays, as in FIG. 3A, also imparts a self-centering interactive force. Referring again to FIG. 3A, when second magnetic array 500 is moved horizontally along the x-axis, peak 511 of its composite magnetic field approaches one of the peaks 411A, 411B of the composite magnetic field of first magnetic array 400, e.g., peak 411B of magnet 402B. As the magnitude of the radial component of the load increases, the distance between the peaks 511, 411B will decrease and the radial component of the repulsive force will increase accordingly. The mechanical energy applied to magnetic apparatus 370 is converted to the potential energy of the interacting magnetic; fields which will have skewed equipotential lines densely packed around the peaks 511, 411B. When the lateral load is removed or decreased, the potential energy of the interacting magnetic fields or at least a portion thereof is converted back to the mechanical energy by repelling second magnetic array 500 toward its centralized equilibrium position and returning the densely packed equipotential lines to their loosely packed state. As will be discussed in greater detail below, the radial stability provided by magnetic apparatus 370 may be applied to confine the motion of the adjacent joint bone portions to a predetermined range, thereby restricting out-of-range displacement thereof.

It will be appreciated by persons skilled in the art that magnetic arrays with different embodiments may also provide above described axial and/or radial stability. For example, the magnetic apparatus may have a first magnetic array having a center magnet and an annular peripheral magnet disposed therearound, wherein the peripheral magnet has greater magnetic intensity than the center magnet. The second magnetic array may be constructed substantially similar to the embodiment of FIG. 3A or may include a center magnet and an annular peripheral magnet disposed therearound, where the center magnet has greater magnetic intensity than the peripheral one. In the alternative, one array may include a weaker center magnet and multiple peripheral magnet disposed around the center magnet. In addition, the magnetic apparatus may also include magnetic arrays forming more than two peaks and/or more than one valley.

Figure 3B:
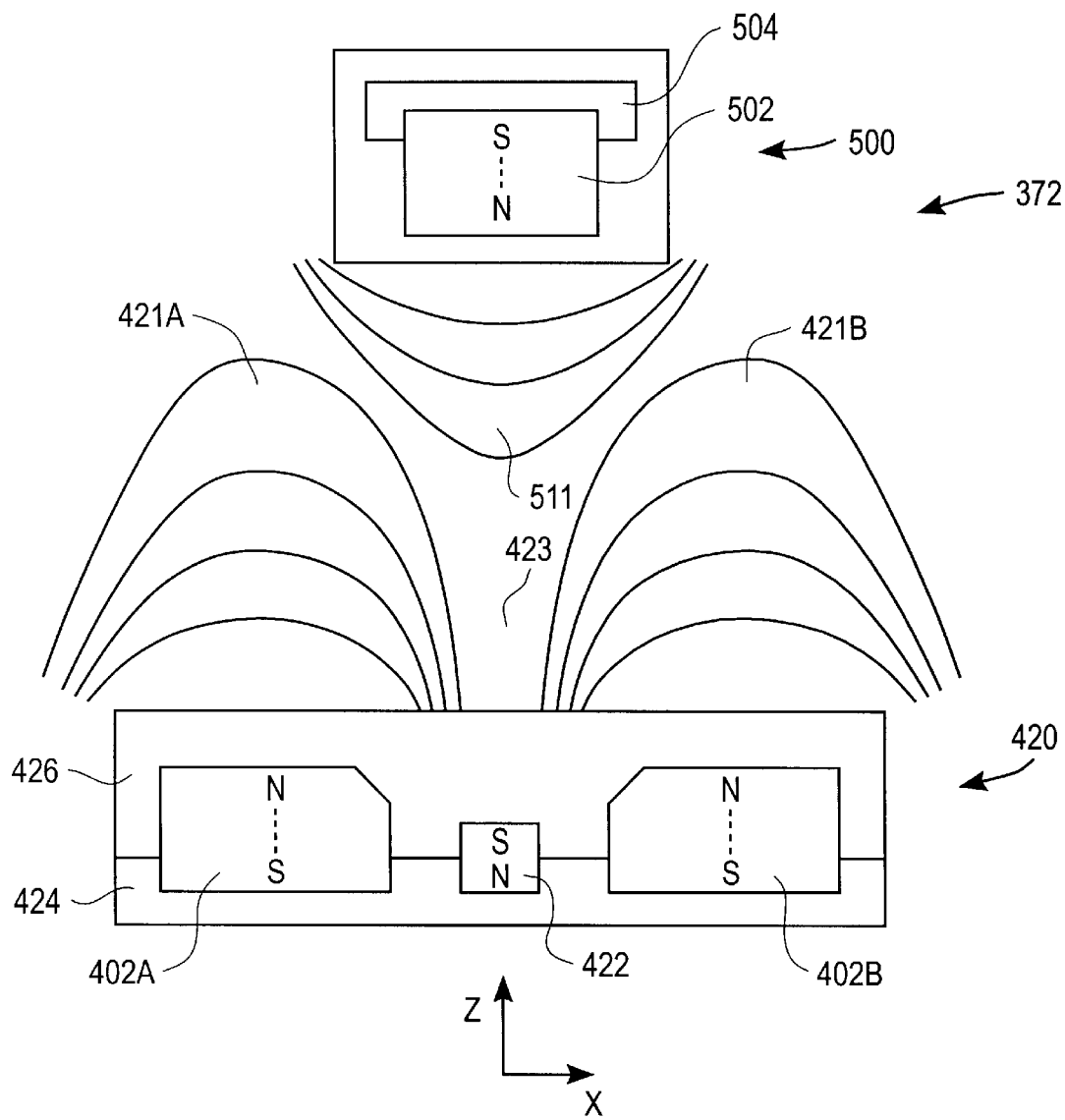
FIG. 3B is a cross-sectional schematic view of another magnetic apparatus for providing stabilizing magnetic field according to an alternate embodiment of the present invention.
Figure 3C:
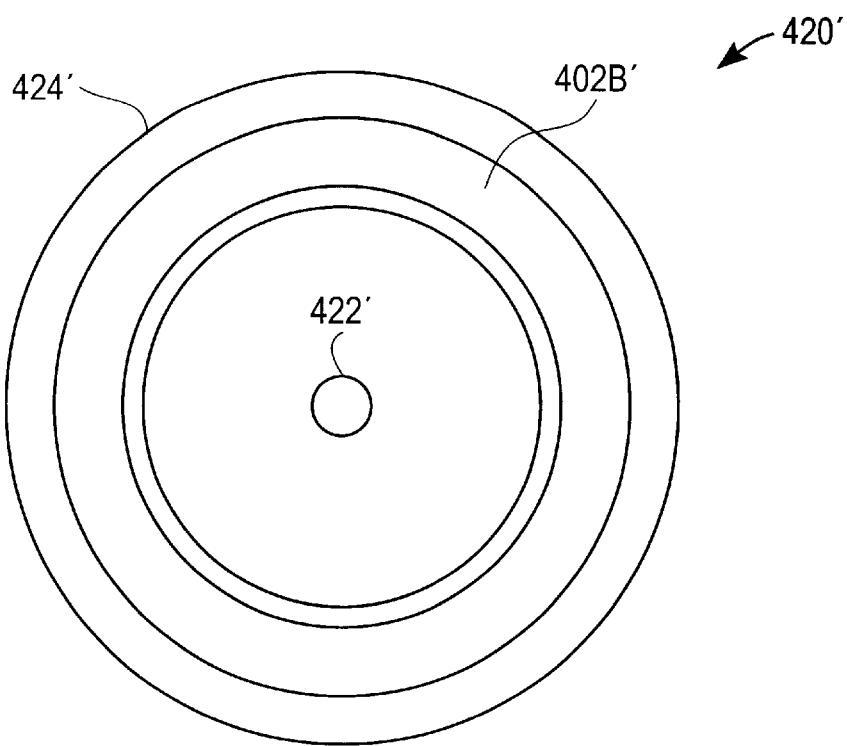
FIGS. 3C and 3D are plan views of alternative embodiments of the array as shown in cross-section in FIG. 3B.
Figure 3D:
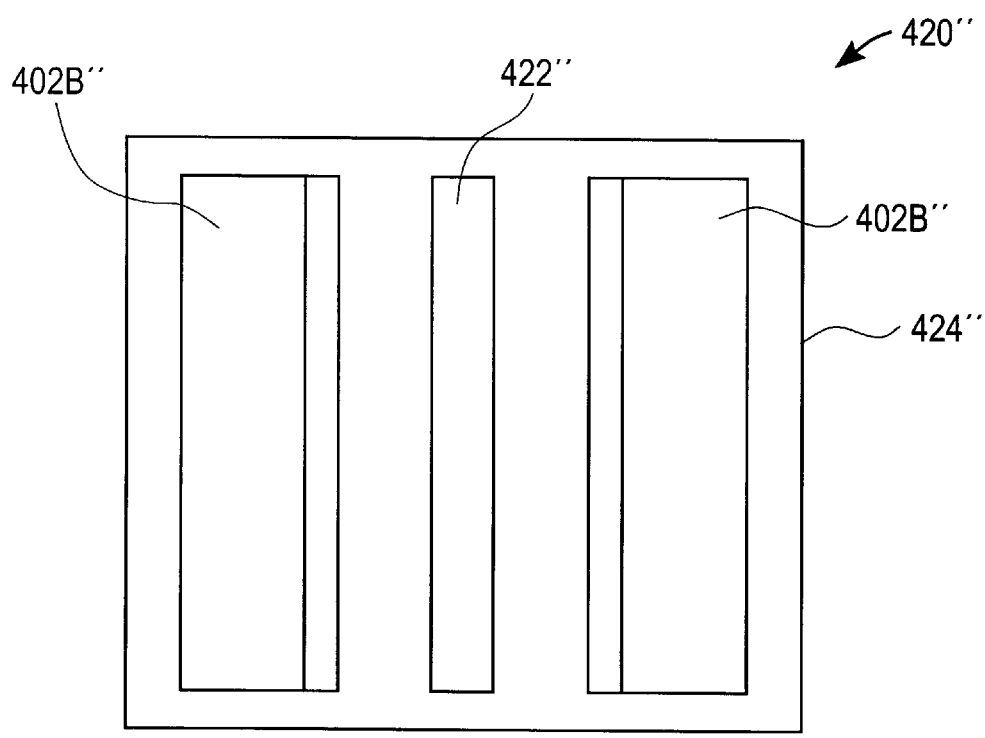

FIG. 3B is a cross-sectional schematic view of another alternative embodiment of the invention showing magnetic apparatus 372 for providing a stabilizing and a repulsive magnetic field according to the present invention. FIGS. 3C and 3D illustrate in plan view alternative embodiments corresponding to the cross-section shown in FIG. 3B wherein first array 420' is an annular configuration and first array 420" is a parallel configuration. (Reference numerals with (') and (") correspond to the same numbers in the description below.)

Magnetic apparatus 372 is provided with the configuration similar to that of apparatus 370 of FIG. 3A, except that first magnetic array 420 includes an additional third magnet 422 disposed between magnets 402A, 402B, secured to housing 424, and sealingly enclosed by the cover 426. Third magnet 422 may be generally smaller and have less magnetic intensity than the other two magnets 402A, 402B. Magnet 422 is also oriented to have its south pole on its upper face opposite to the surrounding magnets. Magnetic flux lines, 421A, 421B emanating from the magnets 402A, 402B are attracted by the south pole of third magnet 422 and directed thereto by a steeper slope or differential descending into the valley region 423. Because of a smaller repulsive force in valley 423, peak 511 of second magnetic array 500 can approach magnetic array 420 or penetrate further into the magnetic field of first magnetic array 420 in its theoretical equilibrium state. This embodiment allows an overlap to a greater extent between peak 511 of second magnetic array 500 with peaks 421A, 421B of first magnetic array 420. Accordingly, any radial movement of the second magnetic array 500 along the x-direction is opposed by stronger radial force component. Therefore, this arrangement may significantly enhance the radial stability as well as the self-aligning capability of the magnetic apparatus 372.

Figure 3E:
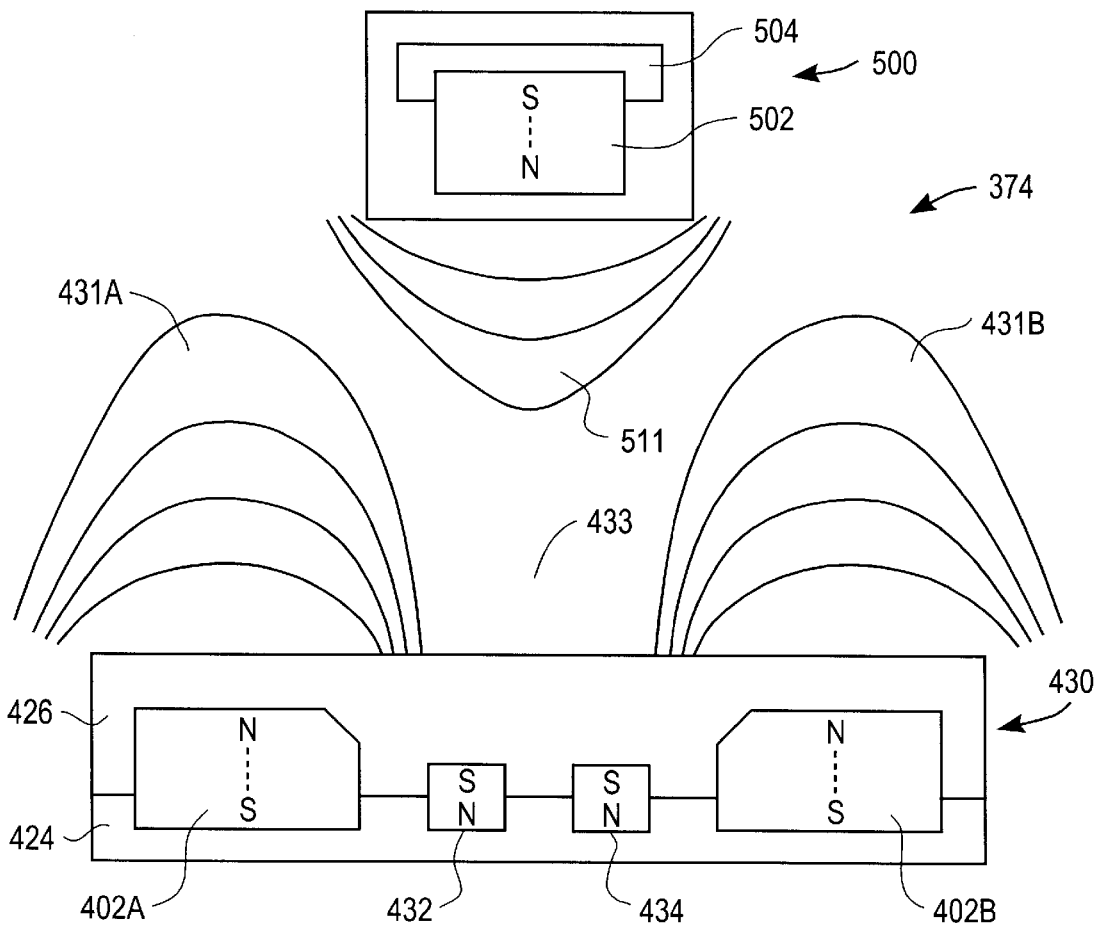
FIG. 3E is a cross-sectional schematic view of a magnetic apparatus for constraining magnetic field according to a further alternative embodiment of the present invention.

FIG. 3E is a cross-sectional schematic view of further alternative magnetic apparatus for constraining motion according to the present invention. Magnetic apparatus 374 has the configuration substantially similar to that of FIG. 3B, except that main magnets 402A, 402B of first magnetic array 430 are separated by a larger distance, and that a third and a fourth magnet 432, 434 are disposed therebetween. Both third and fourth magnets 432,.434 are arranged to have the south poles on their upper faces, facing the opposing array. Accordingly, magnetic flux lines emanating from magnets 402A, 402B are attracted by the south poles of third and fourth magnets 432, 434, increasing the slope of the equipotential lines descending into valley region 433. Compared to valley 423 of FIG. 3B, third and fourth magnets 432, 434 create a deeper and wider valley 433, with weak magnetic intensity. Because of smaller repulsive forces in wider valley 433, peak 511 of the second magnetic array 500 can penetrate the magnetic field of array 430 to a greater degree, but also limit displacement radially from its equilibrium state since it is substantially opposed by neighboring field peaks 431A, 431B of the first magnetic array 430. As will be appreciated by the persons skilled in the art, the precise characteristics and interaction of the magnetic arrays may be controlled by altering the characteristics, in particular the strength of the inner and outer magnets in array 430. For example, the strength or intensity of opposite polarity center magnets 432 and 434 may be increased to provide an attractive force which counterbalances the repulsive force of the outer magnets, thereby providing an apparatus which enhances or increases the stability in a joint rather than only reducing the joint reactive forces. It is appreciated that center magnets 432, 434 may have the same direction of polarity as peripheral magnets 402A, 402B.

Figure 3F:
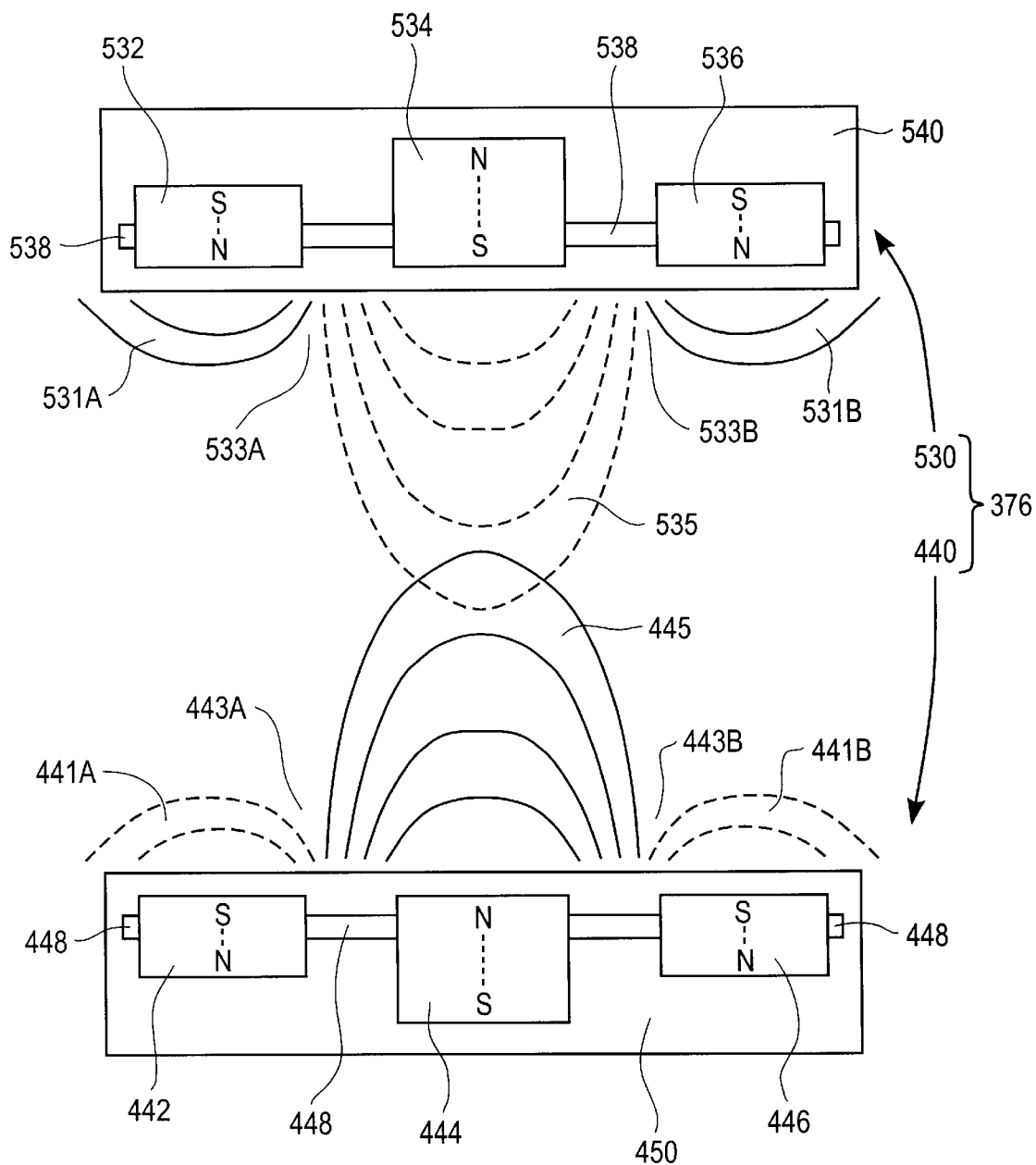
FIG. 3F is a cross-sectional schematic view of another magnetic apparatus for constraining magnetic field according to another alternative embodiment of the present invention.

FIG. 3F is a cross-sectional schematic view of another alternative embodiment of a magnetic apparatus 376 according to the present invention. In this embodiment, first magnetic array 440 includes three magnets 442, 444, 446. Center magnet 444 has its north pole on its upper face and two peripheral magnets 442, 446 have their south poles on the upper face. After being secured to frame 448, all three magnets 442, 444, 446 are further embedded in an outer housing 450 made of implantable material. In general, the center magnet 444 is designed with larger magnetic strength than the peripheral magnets 442, 446. Because the opposite poles are disposed on the same side, the composite magnetic field of the first magnetic array 440 includes two peaks 441A, 441B of the equipotential lines of magnetic fluxes emanating from the south poles of the peripheral magnets 442, 446, and a peak 445 of the equipotential lines of magnetic fluxes with opposite polarity and emanating from the north pole of the center magnet 444. Between peaks 441A, 445, and 441B are also formed two valleys 443A, 443B.

The second magnetic array 530 also includes three magnets 532, 534, 536. Center magnet 534 has its south pole on its upper face and two peripheral magnets 532, 536 have their north poles thereon. All three magnets are also secured to frame 538, arranged to have their upper faces flush with each other, and embedded in an outer housing 540 made of implantable material. Center magnet 534 is also designed to have greater magnetic strength than peripheral magnets 532, 536. Similar to that of first magnetic array 440, the composite magnetic field of second magnetic array 530 includes two peaks 531A, 531B of the equipotential lines originating from the north poles of peripheral magnets 532, 536, and peak 535 of the equipotential lines with the opposite polarity originating from the south pole of center magnet 534. Two valleys 533A, 533B are also formed between peaks 531A, 535 and 531B. The composite magnetic fields of first and second magnetic arrays 440, 530 form two adjacent and interacting magnetic fields. Since the poles of magnets 532, 534, 536 of second magnetic array 530 face the poles of magnets 442, 444, 446 of first magnetic array 430 having opposite polarity, the two arrays are attracted together. The composite fields further interact as a result of the alternative polarity to be drawn together in a specific orientation and to resist rotation with respect to each other.

The embodiment of FIG. 3F provides 1-, 2- or 3-dimensional structural stability to the magnetic apparatus 376. For example, when a static or dynamic load is exerted on the second magnetic array 530, the attractive force of magnetic apparatus 376 prevents displacement of second magnetic array 530 away from the first magnetic array 440. When the magnitude of the external load surpasses a theoretical threshold, second magnetic array 530 may be uncoupled or displaced, generating a gap between magnetic arrays 440, 530. During this displacement, the mechanical energy applied to the magnetic apparatus 376 is converted to the potential energy of the interacting magnetic field in the form of distorted or stretched equipotential lines. When the radial load is removed or decreased, the potential energy of the interacting magnetic field is converted back to the mechanical energy, thereby pushing second magnetic array 530 toward first magnetic array 440, preferably by aligning its center line (axis) with that of first magnetic array 440. As will be discussed in greater detail below, magnetic apparatus 376 thus offers structural stability particularly beneficial in applications such as fracture reduction and treatment for coupling the adjacent bone portions and maintaining the predetermined desired relationship as well as in constraining their 1-, 2-, and/or 3-dimensional motion.

In addition, the embodiment of FIG. 3F provides rotational stability by resisting rotation of the one magnetic array with respect to the other and by providing two or more parallel magnetic forces. When second magnetic array 530 is twisted, the attractive force of the magnetic apparatus 376 prevents rotation of the second magnetic array 530 about the first magnetic array 440. When the magnitude of the external load surpasses the threshold, second magnetic array 530 may be rotated, causing opposite poles of the opposing array 530 to interact and repel each other. During rotation, the mechanical energy applied to the magnetic apparatus 376 is converted to the potential energy of the interacting magnetic fields in the form of distorted or stretched equipotential lines. If the external load further increases in its magnitude, the second magnetic array 530 is further rotated and the distance between the like poles of first and second magnetic arrays 440, 530 generate the repulsive force opposing the rotation or translation. When the load is decreased or removed, the potential energy of the interacting magnetic field is converted back to the mechanical energy, allowing second magnetic array 530 to revert back to its equilibrium positioned with first magnetic array 440. As will also be discussed in greater detail below, magnetic apparatus 376 is particularly beneficial in coupling the adjacent bone portions and in preventing their 1-, 2-, and/or 3-dimensional rotation, as is often required in fracture reduction and stabilization.

The magnetic apparatus, magnetic arrays, and magnets therefor described hereinabove are designed and manufactured based on variety of factors, such as the anatomical part that needs to be treated, the pathologic or etiologic origins thereof, the physiological characteristics of patients, and/or the decisions made by medical experts. Once the orthopedic surgeon decides the primary purpose of orthopedic treatment, e.g., providing one or more of axial, radial, structural, and/or rotational stability, he or she may choose from a group of pre-manufactured implants according to the invention to provide appropriate characteristics that generate the contour and distribution pattern of equipotential lines and provide preferred ranges of attractive and/or repulsive force(s) associated therewith.

Various factors may effect the topographic contour and/or distribution pattern of the equipotential lines, configuration and/or location of the peaks and the valley of the equipotential lines, and the dynamic properties thereof (e.g., the packing state). Examples of such factors may include, but are not limited to, material, shape, size, polarity, strength, orientation, and distribution pattern of the magnets. Further examples may include orientation of the magnetic axis, number and/or distribution pattern of the poles on each side of the magnetic arrays, presence of insulating material around or between the magnets, and presence of symmetric, axial-symmetric or non-symmetric distribution of the magnets in the magnetic arrays (or a plurality of magnetic arrays themselves). For example, the magnetic array may include cylindrical, rectangular, annular, conical, spherical, slab-like, bar-shaped, U-shaped, and/or C-shaped magnets, and/or magnets with other geometric shapes and/or sizes suitable for the specific treatment. Magnetic intensity of a particular magnet may be altered resulting in the equipotential lines being shifted or skewed. Similar results may be obtained by changing relative positions of the magnets. In addition, by changing the configuration and orientation of one magnet with respect to the others, the equipotential lines may be altered and distribution thereof skewed in any desirable direction. For example, instead of the bell-shaped contours described in FIGS. 1C, 1E, 1F, and 1H, the equipotential lines may be arranged to have an inverse U-shaped distribution pattern. Preferably these contours will be three dimensional, such as paraboloid or rotated sinusoid as previously described in order to permit one three dimensional field to penetrate and be constrained by the other.

The composite magnetic field of a magnetic array may be quantitatively assessed utilizing the governing equations (e.g., differential equations of divergence and curl of a magnetic flux density vector) of magnetostatics or magnetodynamics, with appropriate boundary conditions and delineated properties of the conducting medium. The composite magnetic field of a complicated magnetic array may also be analytically estimated by approximating the terms of the governing equations and/or the boundary conditions. Alternatively, such solutions and/or estimations may also be obtained by numerical methods such as finite element, finite difference or boundary element analysis or by computer simulation using software which is commercially available, for example, LORENTZ from Integrated Engineering Software, Winnipig, Manatoba, CANADA. Accordingly, specific contour- or pattern-determining factors described hereinabove can be optimized by a computer modeling and analysis and then selected to provide the desired function by one skilled in the art.

Conversely, the configuration of the magnets, the magnetic arrays, and/or the magnetic apparatus may be deduced from the predetermined distribution pattern of magnetic flux lines and/or equipotential lines of composite magnetic fields. In theory, the preferred configuration of the magnets and magnetic array can be obtained by finding the solution of the governing equations of magnetostatics or magnetodynamics with the desired predetermined composite magnetic fields as the boundary conditions. Solutions to such equations can be very complex. It is preferred that at least a portion of the solution be known in advance, and the analytical, numerical, and/or computer simulation method resorted to for obtaining specific details of the solutions for the governing equations. For example, in treating various joint disorders, the surgeon may decide to provide the axial and radial stability to the adjacent bone portions by using two magnetic arrays, each including two concentric magnets with the north poles in opposition. The surgeon may also determine the dimensions of the magnetic array based on the shape and size of the adjacent joint bone portions into which the magnetic arrays are to be implanted. By incorporating the detailed information into the boundary conditions and/or by assuming the basic functional characteristics of the solution (e.g., exponential, hyperbolic or polynomial terms), the analytical, numerical, and/or computer simulation may yield a more practical solution.

Alternatively, various sets of standardized orthopedic magnetic apparatus may be provided so that the surgeon may select from a set of apparatus that provides options that are suitable to the particular purpose of the orthopedic treatment. For example, depending on whether the principal purpose of orthopedic treatment is to provide axial, radial, structural, and/or rotational stability and whether the dominant driving force is the repulsive or attractive force, the surgeon may select the magnetic arrays including the magnets with desirable shapes, sizes, configuration, and/or magnetic intensity. The standardized sets may further be provided based on other criteria such as dimensions or space available for implanting the orthopedic magnetic arrays and/or the methods of coupling and securing the magnetic arrays to the adjacent bone portions.

In yet another alternative, universal orthopedic magnetic apparatus may be provided to allow the surgeon to customize the orthopedic magnetic apparatus based on the particular purpose of the orthopedic treatment. For example, a manufacturer may provide the surgeon an inventory of standardized magnets having various shapes, sizes, and/or intensities, and another inventory list of housings with universal receptacles. The surgeon or the appropriate representative may select magnets which best suit the purpose of the orthopedic treatment and position the magnets on the universal housing, thereby creating a customized magnetic array. After the magnets are sealingly enclosed by a universal enclosure, embedded or incased in an outer housing, the magnetic array thus prepared will be ready for implantation.

EXAMPLE

Figures 4A, 4E:
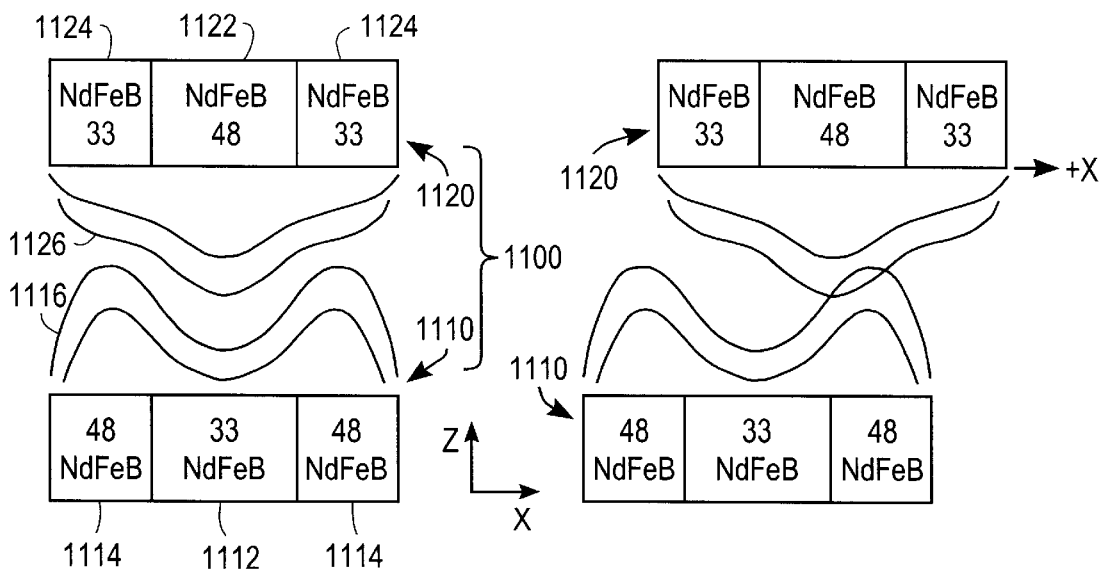
FIG. 4A is a schematic representation illustrating the interaction between two magnetic arrays as described in the Example.
FIG. 4E is a schematic representation further illustrating the interaction between the magnetic arrays shown in FIG. 4A.

The following example represents the results of a computer model of a basic array design incorporating the fundamentals of the present invention. A computer simulation was performed to determine the magnitude of the repulsive vertical and radial force components of a representative magnetic arrays. As illustrated in FIG. 4A, apparatus 1100 includes first magnetic array 1110 and a second magnetic array 1120, where both arrays include the cylindrical center magnets 1112, 1122 positioned inside annular magnets 1114, 1124. The center magnets for each array were chosen to be one inch in diameter. The annular magnets were chosen to have an O.D. of two inches and an I.D. of one inch. Each array was one inch thick. In second array 1120, central magnet 1122 was made of NdFeB 48 and outer annular magnet 1124 was made of NdFeB 33. First array 1110 had the same configuration except that the magnet materials were reversed such that the stronger NdFeB 48 was at the outside. Both the first and second magnetic arrays were oriented such that the same poles (e.g., north poles) were disposed facing each other. Therefore, first magnetic array 1110 generated the first composite magnetic field having approximately "M"-shaped (or cup shape in three dimensions) equipotential lines 1116, while the second magnetic array 1120 created the second composite magnetic field having approximately "V"-shaped (or paraboloid shape in three dimensions) equipotential lines 1126. As a result, first and second magnetic arrays 1110, 1120 tended to be forced apart from each other by the repulsive force generated therebetween.

Figure 4F:
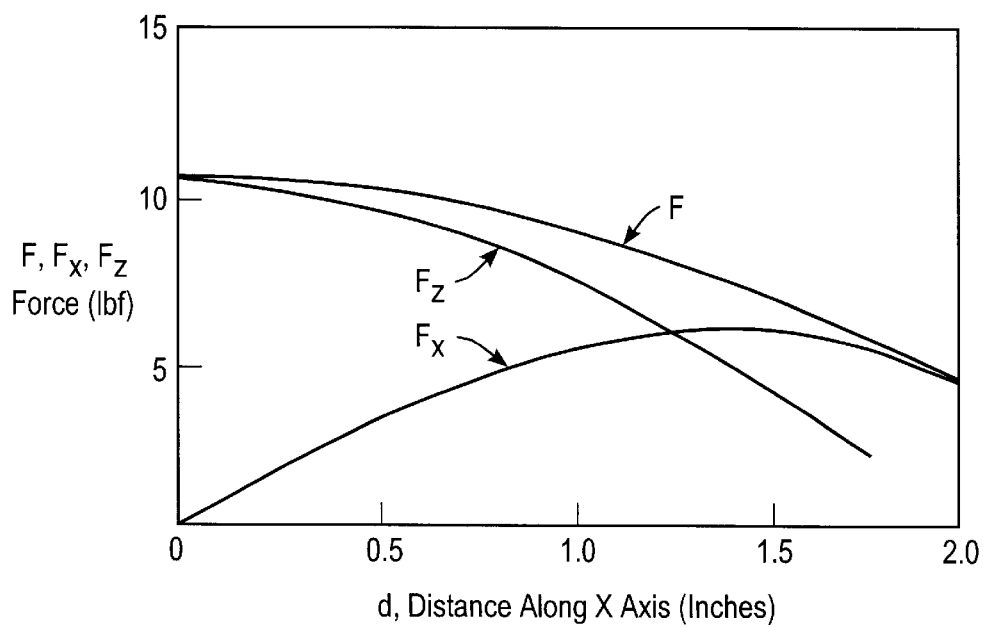
FIG. 4F is a plot of forces resulting from the interaction of magnetic arrays as explained in the Example.
Figure 4B:
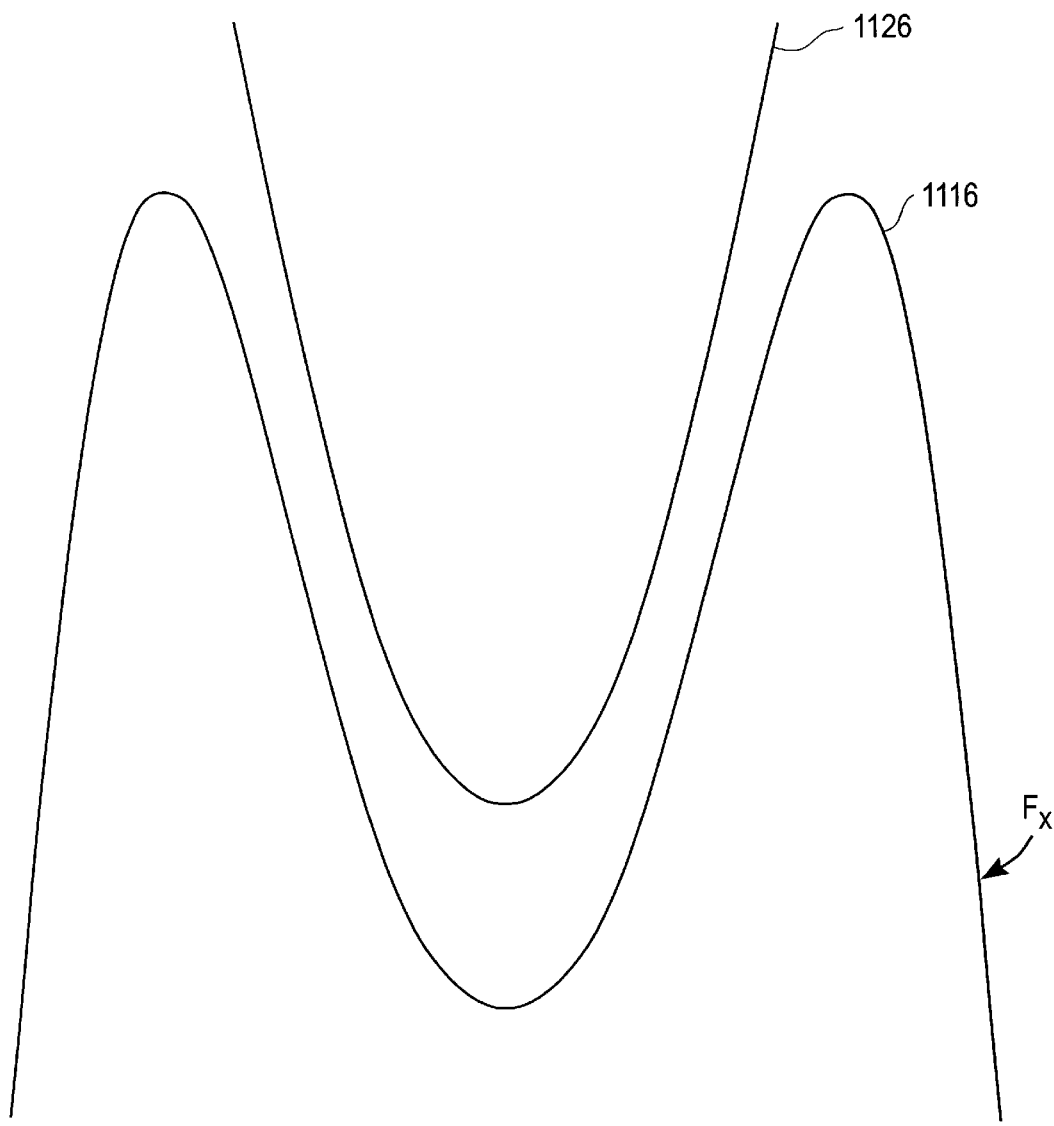
FIG. 4B is a graphical representation of the cooperating magnetic fields generated by the magnetic arrays shown in FIG. 4A.
Figure 4C:
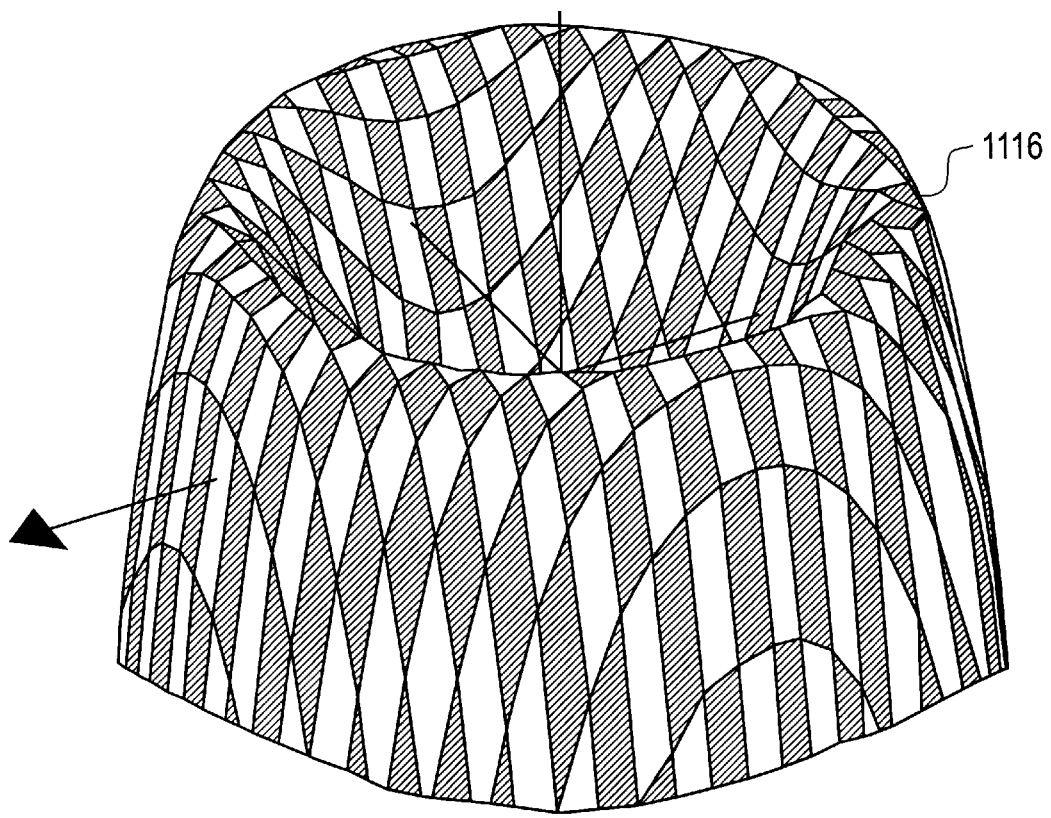
FIG. 4C is a graphical representation in three dimensions of the magnetic field generated by the lower magnetic array in FIG. 4A.
Figure 4D:
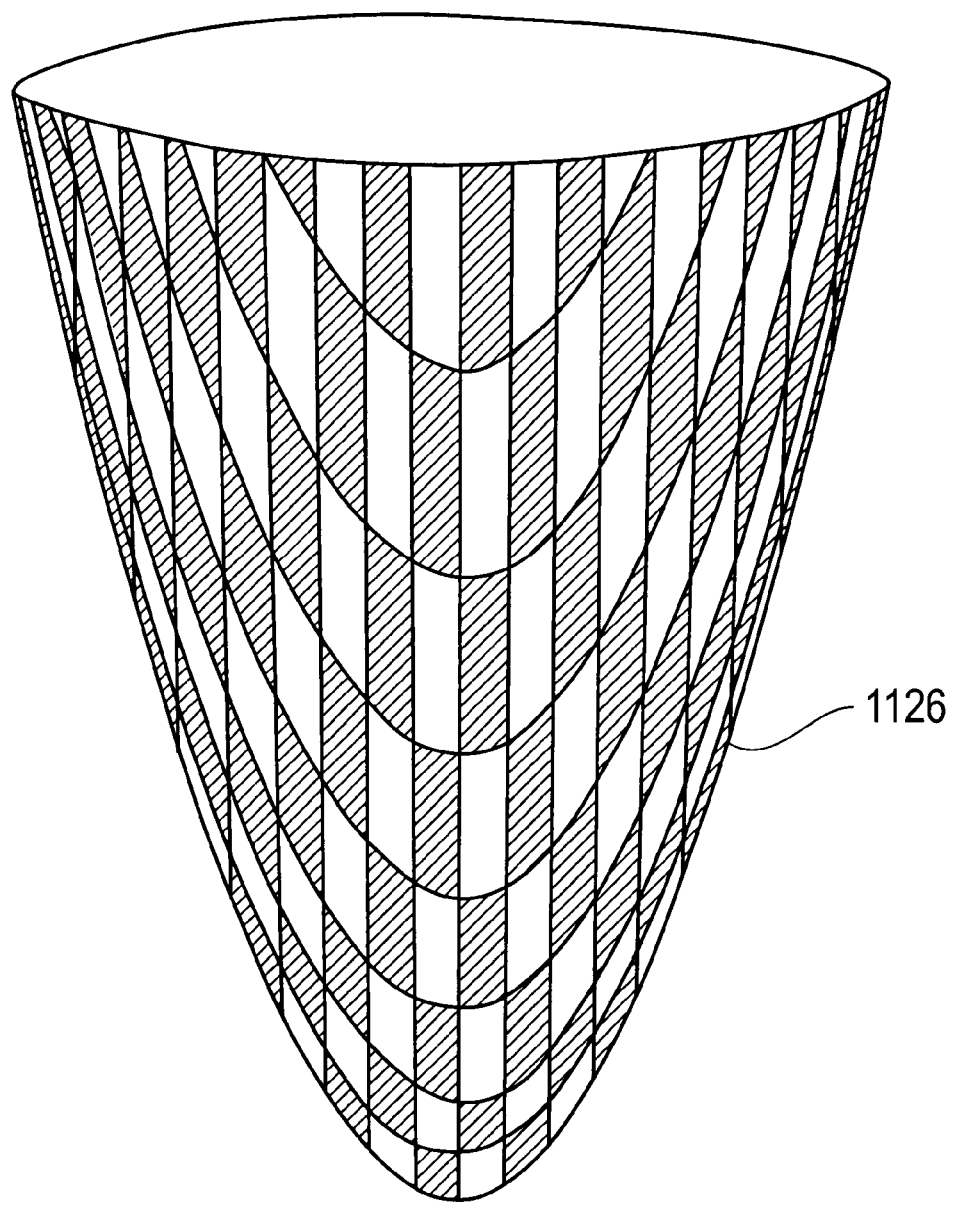
FIG. 4D is a graphical representation in three dimensions of the magnetic fields generated by the upper magnetic array in FIG. 4A.

The magnetic fields generated by the arrays are represented graphically in FIGS. 4B, 4C and 4D. For magnetic array 1120, a cross-section of the magnetic field and equipotential lines 1126 is approximated by the formula, $y=3x^2$ and for magnetic array 1110, a cross-section of the magnetic field and equipotential lines 1116 is approximated by the formula, $y=3 \sin(x^2)$. In FIG. 4B, the interacting magnetic fields are represented as positioned approximately 0.75" apart in the vertical direction to illustrate how upper magnetic array 1120 and its magnetic field 1126 may be retained by the cup shaped magnetic field 1116 of lower magnetic array 1110. (This spacing is illustrative only and may not represent actual spacing.) FIG. 4C illustrates a perspective view of the magnetic field 1116 generated by lower magnetic array 1110 in three dimensions, obtained by the formula, $z=3\sin(x^2+y^2)$. Similarly, FIG. 4D illustrates a perspective view of the magnetic field 1126 generated by upper magnetic array 1120 in the three dimensions, obtained by the formula, $z=3(x^2+y^2)$.

To illustrate the interaction between the cooperating magnetic fields of the two arrays, second magnetic array 1120 was positioned approximately one inch above first magnetic array 1110. Second magnetic array 1120 was then moved in the positive x-direction while maintaining the same vertical distance therebetween as depicted in FIG. 4E. Commercial software was used to simulate the variations in magnitude of the net repulsive force and its radial and axial components as the relationships between the two magnetic arrays of the apparatus were changed.

FIG. 4F is a plot of the axial and radial repulsive force components generated from the sample magnetic apparatus as the upper array was moved radially. Symbols "F," "$F_X$," and "$F_Z$," represent the magnitude of the total net repulsive force, the magnitude of the force component in the radial direction (x-direction), and the magnitude of the force component in the vertical direction (z-direction), respectively, where the net force, F, is calculated as a square root of a sum of squares of $F_X$ and $F_Z$. The radial offset distance between the central axes of magnetic arrays 1110, 1120 is denoted by a symbol "d" along the abscissa. ($F_Y$ was set according to the conditions of the model to be ~0).

As shown in FIG. 4F, magnetic arrays 1110, 1120 do not exert radial force when their center lines are aligned in the x-z plane (i.e., where d=0). As the second magnetic array is displaced from the aligned equilibrium position in the x-z plane, the lateral force component ($F_X$) increases while the net vertical force component ($F_Z$) decreases. When d is approximately +/−1.2 in., the radial force component ($F_X$) equals the vertical force component ($F_Z$) and surpasses it thereafter. When (d) is 2.0 in., more than 95% of the net repulsive (F) are attributed to the radial force component ($F_X$).

This simulation demonstrates the interaction between cooperating magnetic fields of magnetic arrays according to the invention. In particular, in this example the self-centering and retention features of properly designed arrays are demonstrated.

Figure 5A:
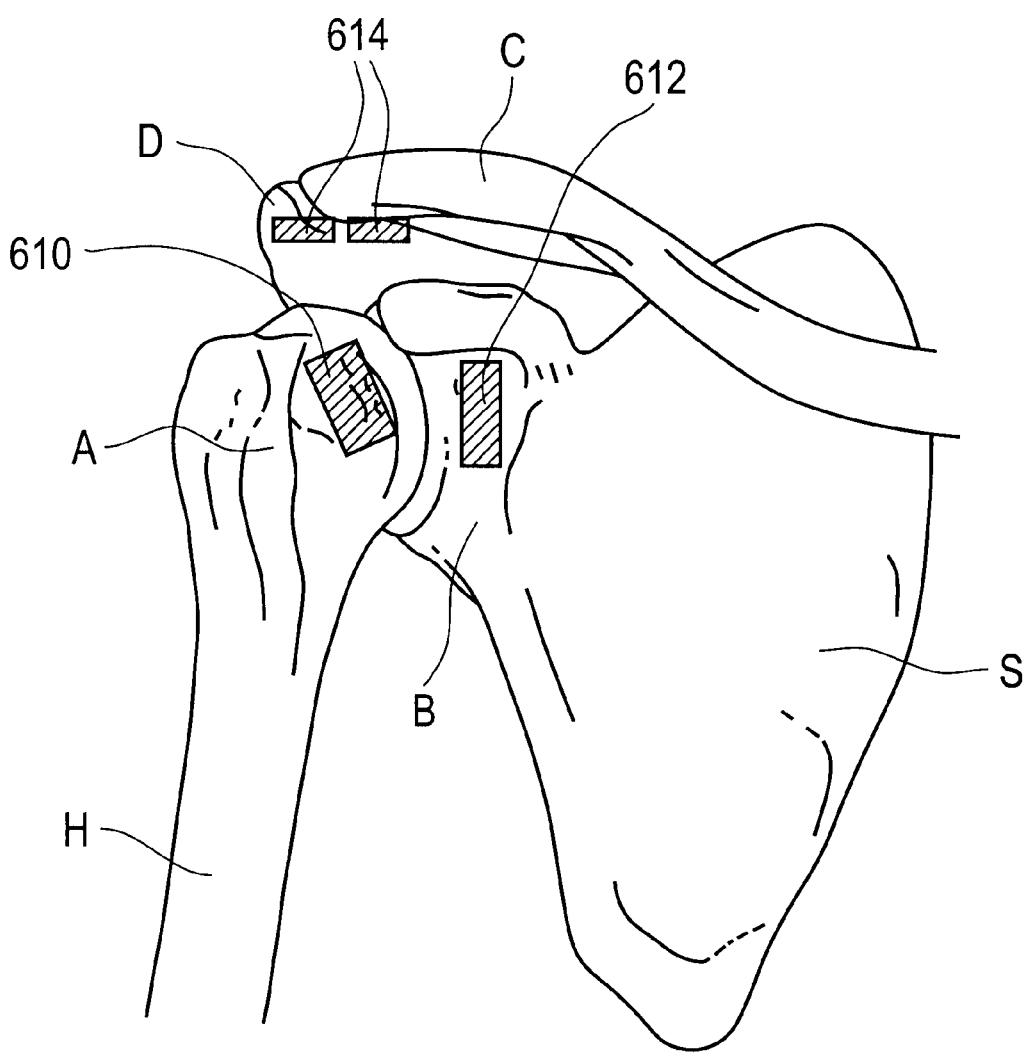
FIGS. 5A and 5B are diagrammatic representations of alternative embodiments of the present invention directed to joint treatment or stabilization.
Figure 5B:
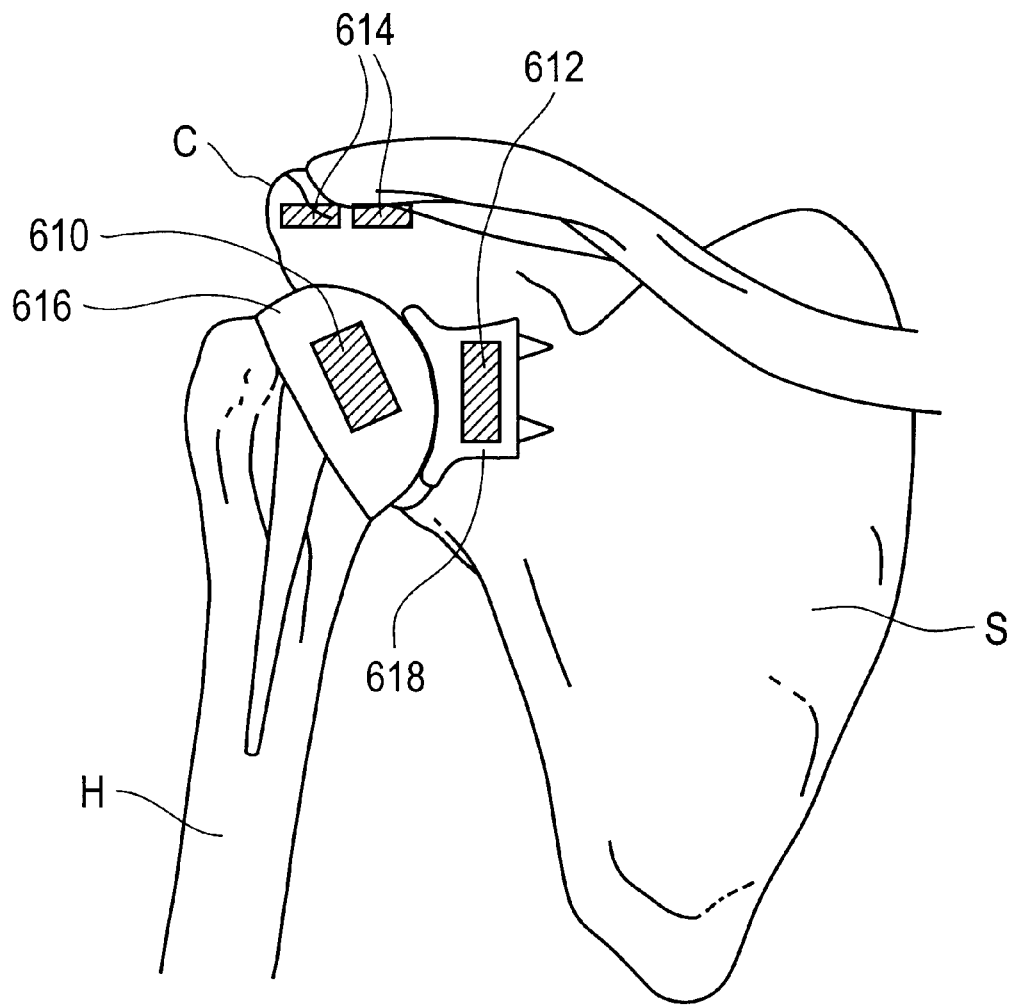

By way of further example, FIGS. 5A and 5B illustrate alternative embodiments for treatment of shoulder conditions utilizing magnetic array implants according to the present invention. As depicted in FIG. 5A, the shoulder joint includes the humerus (H), scapula (S) and the clavicle (C). Matched magnetic arrays 610, 612, and 614 according to the present invention are placed in the humeral head (A), the glenoid (B), and the acromion (D), respectively. The magnetic arrays may be designed to provide a significant repulsive force between the adjacent bone portions to reduce or prevent contact and wear of the joint components. Less significant attractive forces between the magnets may be used to stabilize the bones of the shoulder joint in an anatomical or near-anatomical configuration. The attractive forces of the matched magnetic arrays will tend to compensate for any forces that are disruptive to the normal configuration of the bones in the shoulder joint. Centralizing forces stabilize the bones of the shoulder joint by keeping them aligned in their functionally anatomical position. For example, magnetic arrays 610 and 612 may comprise a pair of arrays having a similar design to that of magnetic arrays 1110 and 1120 as described in the Example above. The shape of the magnetic field created by array 610 would cooperate with the shape of the magnetic field generated by array 612 such that interaction between the magnetic fields would provide the necessary centralizing forces. To the extent attractive forces are used in a particular implementation, such attractive forces may be created and controlled as described in connection with the alternative embodiments shown in FIGS. 3B and 3E, above. This embodiment also illustrates that not all magnets in an array need act in the same plane. In particular, magnetic array 610 includes magnets acting upward to cooperate with array 614 positioned in the acromion and further includes magnets acting generally laterally to cooperate with array 612 positioned in the glenoid.

FIG. 5B illustrates a further alternative embodiment wherein magnetic arrays according to the present invention are utilized to augment the design of current prosthetic elements. As shown in FIG. 5B, magnetic array 610 is positioned within humeral head replacement prosthesis 616. Likewise, magnetic array 612 is positioned within glenoid replacement prosthesis 618. The cooperation and effect of the magnetic arrays are as described above. Prostheses 616, 618, may be implanted according to known techniques. Utilizing magnetic arrays according to the present invention with known prostheses may prevent or decrease wear and increase stability, thereby prolonging prosthesis life.

Figure 6:
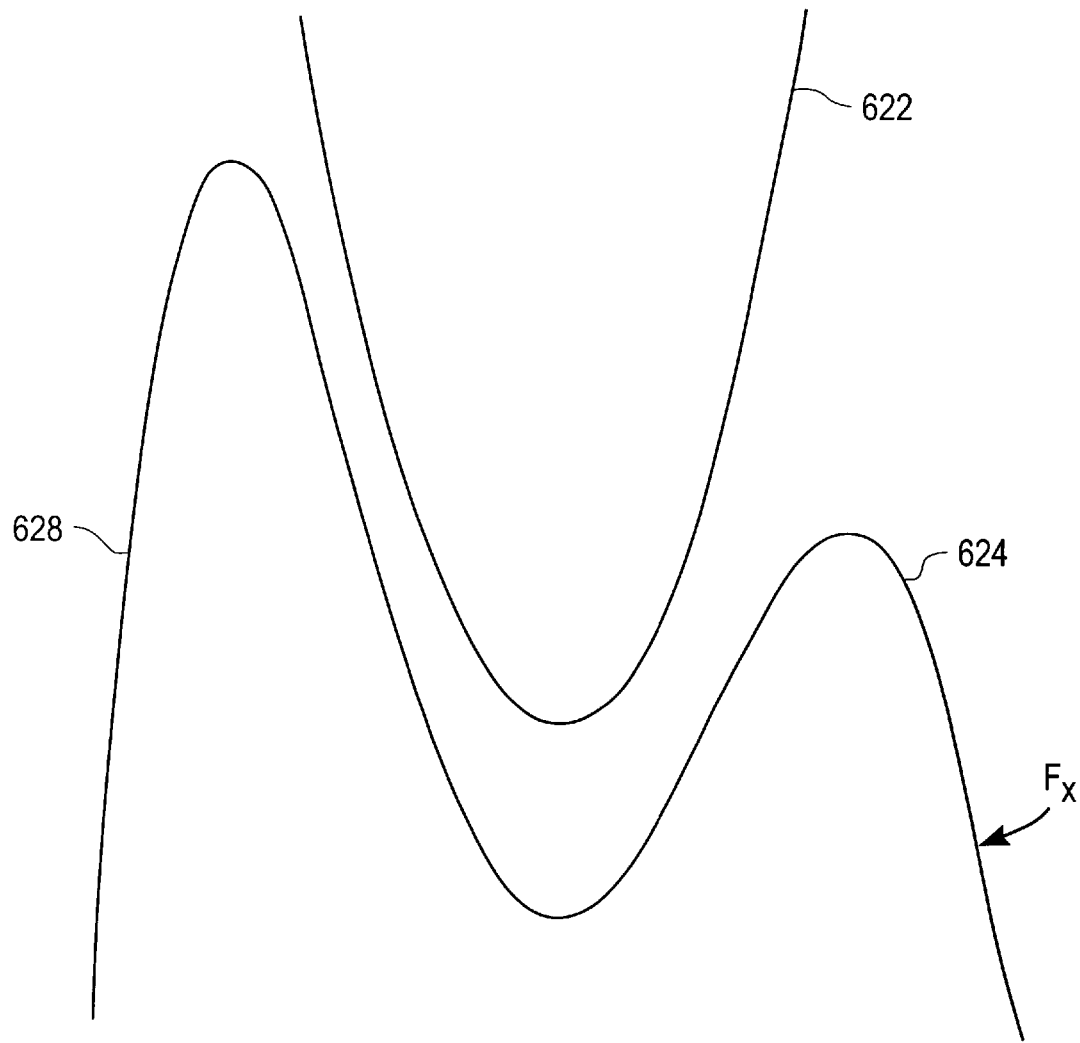
FIG. 6 is a graphical representation of cooperating magnetic fields in an alternative embodiment of the invention.

As previously mentioned, asymmetric arrays may be utilized to address particular problems or situations faced by surgeon. For example, in order to increase anterior stability in a shoulder joint application, a surgeon may select magnetic arrays having cooperating fields 622 and 624 as shown in FIG. 6. In this embodiment, magnetic field 624 is formed asymmetrically to provide increased translational stability along axes orthogonal to the magnetic axis in region 628. This may be accomplished, e.g., by utilizing a magnetic array such as array 10 shown in FIG. 1A and by altering two to four of the peripheral magnets to have weaker or stronger magnetic intensity.

Figure 7:
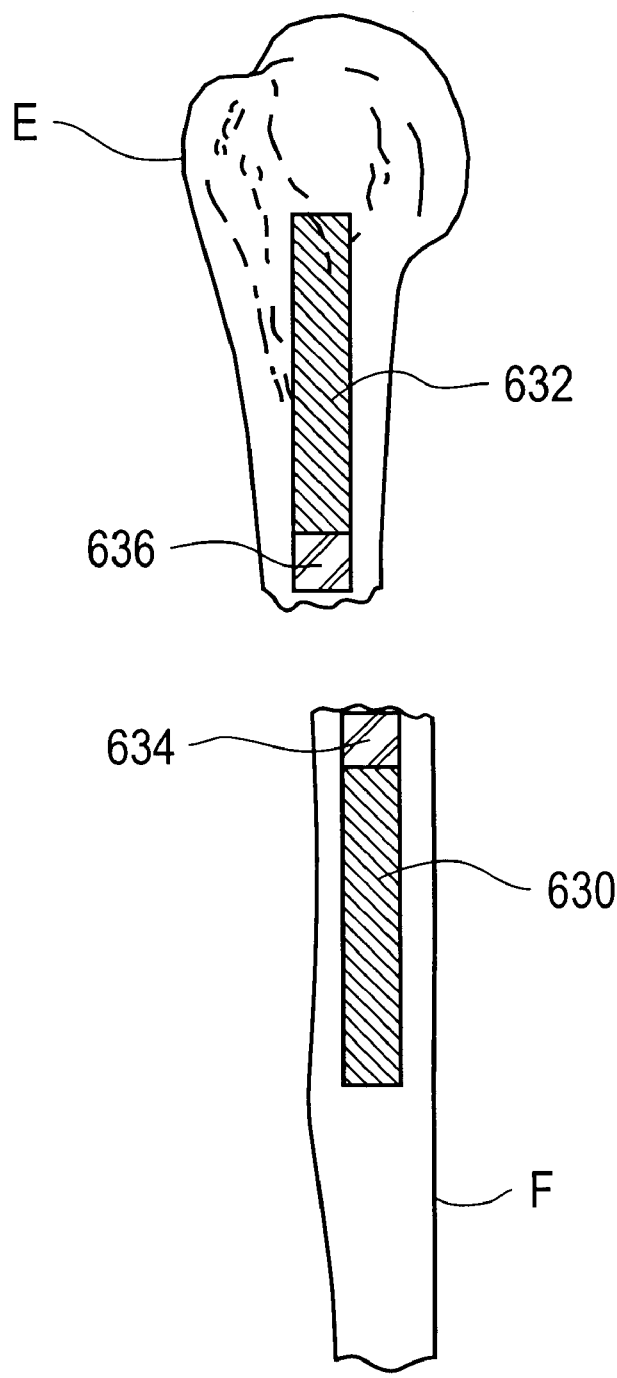
FIG. 7 is a diagrammatic representation of a further alternative embodiment of the present invention for fracture treatment and reduction.

FIG. 7 illustrates a further alternative embodiment of the present invention wherein magnetic arrays according to the invention are utilized for fracture reduction and stabilization. In this example, a long bone is fractured into two bone portions (E, F). A fracture reducing implant is provided in two components formed as intramedullary rod portions 630 and 632. Disposed at one end of each rod portion are magnetic arrays 634 and 636. In such an arrangement, the attractive forces between magnetic arrays 634 and 636 align and stabilize the bone portions resulting from the fracture. The paired magnetic arrays may also allow micro-motion between the fragments and set up a magnetic field in the environs of the fracture, which may be favorable to promoting fracture healing. An example of a preferred arrangement of arrays for this application would be such as that shown in FIG. 3F, above.

It is to be understood that while illustrative embodiments of the invention have been shown and described herein, various changes and adaptions in accordance with the teachings of the invention will be apparent to those of skill in the art. Such changes and adaptions nevertheless are included within the spirit and scope of the invention as defined in the following claims.

What is claimed is:

1. An apparatus for treating adjacent bone portions, comprising:
    a first magnetic array configured and dimensioned to be secured to a first adjacent bone portion and to provide a first magnetic field having first predetermined field characteristics; and
    a second magnetic array configured and dimensioned to be secured to a second adjacent bone portion and to provide a second magnetic field having second predetermined field characteristics,
    wherein said first and second predetermined field characteristics are selected to interact such that the magnetic arrays cooperate to urge said adjacent bone portions into the predetermined desired relationship and constrain relative motion between said bone portions in at least two dimensions,
    one of said magnetic arrays comprises at least two magnets configured and dimensioned to provide a composite magnetic field having said predetermined field characteristics,
    another of said magnetic arrays comprises at least one magnet configured and dimensioned to provide another of said predetermined field characteristics and said composite magnetic field is asymmetrical.

2. An apparatus for treating adjacent bone portions, comprising:
    a first magnetic array configured and dimensioned to be secured to a first adjacent bone portion and to provide a first magnetic field having first predetermined field characteristics; and
    a second magnetic array configured and dimensioned to be secured to a second adjacent bone portion and to provide a second magnetic field having second predetermined field characteristics,
    wherein said first and second predetermined field characteristics are selected to interact such that the magnetic arrays cooperate to urge said adjacent bone portions into the predetermined desired relationship and constrain relative motion between said bone portions in at least two dimensions,
    at least one of said magnetic arrays comprises a plurality of individual magnets secured in a housing in a predetermined relationship to one another and defining an upper face and a lower face, and said magnets are arranged with parallel magnetic axes and uniform polarity at the faces of said array.

3. An apparatus for treating adjacent bone portions, comprising:
    a first magnetic array configured and dimensioned to be secured to a first adjacent bone portion and to provide a first magnetic field having first predetermined field characteristics; and
    a second magnetic array configured and dimensioned to be secured to a second adjacent bone portion and to provide a second magnetic field having second predetermined field characteristics,
    wherein said first and second predetermined field characteristics are selected to interact such that the magnetic arrays cooperate to urge said adjacent bone portions into the predetermined desired relationship and constrain relative motion between said bone portions in at least two dimensions,
    at least one of said magnetic arrays comprises a plurality of individual magnets secured in a housing in a predetermined relationship to one another and defining an upper face and a lower face, and said magnets comprise a central magnet with a plurality of peripheral magnets arranged there around.

4. An apparatus for treating adjacent bone portions, comprising:
    a first magnetic array configured and dimensioned to be secured to a first adjacent bone portion and to provide a first magnetic field having first predetermined field characteristics; and
    a second magnetic array configured and dimensioned to be secured to a second adjacent bone portion and to provide a second magnetic field having second predetermined field characteristics,
    wherein said first and second predetermined field characteristics are selected to interact such that the magnetic arrays cooperate to urge said adjacent bone portions into the predetermined desired relationship and constrain relative motion between said bone portions in at least two dimensions,
    at least one of said magnetic arrays comprises a plurality of individual magnets secured in a housing in a predetermined relationship to one another and defining an upper face and a lower face, and said magnets comprise plural central magnets surrounded by a plurality of peripheral magnets.

5. An apparatus for treating adjacent bone portions, comprising:

a first magnetic array configured and dimensioned to be secured to a first adjacent bone portion and to provide a first magnetic field having first predetermined field characteristics; and a second magnetic array configured and dimensioned to be secured to a second adjacent bone portion and to provide a second magnetic field having second predetermined field characteristics, wherein said first and second predetermined field characteristics are selected to interact such that the magnetic arrays cooperate to urge said adjacent bone portions into the predetermined desired relationship and constrain relative motion between said bone portions in at least two dimensions, and at least one said magnetic array comprises a first annular magnet defining an open center.

6. An apparatus for treating adjacent bone portions, comprising:

a first magnetic array configured and dimensioned to be secured to a first adjacent bone portion and to provide a first magnetic field having first predetermined field characteristics; and a second magnetic array configured and dimensioned to be secured to a second adjacent bone portion and to provide a second magnetic field having second predetermined field characteristics, wherein said first and second predetermined field characteristics are selected to interact such that the magnetic arrays cooperate to urge said adjacent bone portions into the predetermined desired relationship and constrain relative motion between said bone portions in at least two dimensions, and at least one said magnetic array comprises a first annular magnet defining an open center, said magnetic array further comprises a second magnet disposed within said open center, said first and second magnets having different magnetic intensities.

7. An apparatus for treating adjacent bone portions, comprising:

a first magnetic array, including at least two magnets, configured and dimensioned to be secured to a first adjacent bone portion and to provide a first, composite magnetic field having first predetermined field characteristics, said field characteristics including magnetic flux lines defining at least one region of first magnetic intensity bounded by at least one region of second magnetic intensity; and a second magnetic array configured and dimensioned to be secured to a second adjacent bone portion and to provide a second magnetic field having second predetermined field characteristics, said field characteristics including magnetic flux lines defining at least one region of third magnetic intensity, wherein the regions of magnetic intensity interact to urge said adjacent bone portions into a predetermined desired relationship and constrain relative motion between said bone portions in at least two dimensions;

said first and second magnetic arrays are configured and dimensioned secured to said adjacent bone portions at a predetermined distance apart along a first axis, and are oriented with respect to each other in a predetermined relationship along at least a second axis different from said first axis;

said second magnetic array includes at least one magnet, with said at least two magnets of the first array and said at least one magnet of the second array being arranged with common poles in opposition to produce a predetermined repulsive force therebetween at said predetermined distance; and relative movement between said arrays along said second axis away from said predetermined relationship is resisted by interaction between said magnetic fields in said regions of second and third intensity.

8. An apparatus for treating adjacent bone portions, comprising:

a first magnetic array, including at least two magnets, configured and dimensioned to be secured to a first adjacent bone portion and to provide a first, composite magnetic field having first predetermined field characteristics, said field characteristics including magnetic flux lines defining at least one region of first magnetic intensity bounded by at least one region of second magnetic intensity; and a second magnetic array configured and dimensioned to be secured to a second adjacent bone portion and to provide a second magnetic field having second predetermined field characteristics, said field characteristics including magnetic flux lines defining at least one region of third magnetic intensity, wherein the regions of magnetic intensity interact to urge said adjacent bone portions into a predetermined desired relationship and constrain relative motion between said bone portions in at least two dimensions;

each said array has an opposing face and a back face, and comprises at least two magnets, each magnet having a polar axis;

the magnets of each array are aligned with their polar axes substantially parallel such that the poles of each magnet are adjacent and disposed at the faces of each array; and said arrays are adapted to be secured to adjacent bone portions opposite to each other with the opposing faces facing together and in a predetermined position with respect to each other along a first axis substantially parallel to said polar axes and along at least a second axis different from said polar axes.

9. The apparatus according to claim 8, wherein:

the magnets of each array are aligned with opposite poles positioned on the opposing faces;

the predetermined position along the first axis comprises the first and second array being at least substantially in contact along the opposing faces;

interaction between said magnetic fields resists relative rotation between said arrays.

10. The apparatus according to claim 8, wherein:

the magnets of each array are aligned with the same poles positioned on the opposing faces;

the predetermined distance along the first axis comprises a predetermined spacing;

interaction between the magnetic fields resists reduction of the predetermined spacing and resists movement away from the predetermined position along the second axis while permitting at least one of rotation, flexion and extension.

11. The apparatus according to claim 10, wherein at least one said magnetic array further comprises at least one magnet disposed in said array with an opposite pole positioned on the opposing face.

12. A method of treating adjacent bone portions, comprising:

securing a first magnetic array to a first adjacent bone portion to provide a first composite magnetic field therearound;

securing a second magnetic array to a second adjacent bone portion to provide a second composite magnetic field therearound; and disposing said first and second magnetic arrays in opposition to each other to simultaneously generate both repulsive and attractive forces, thereby urging said adjacent bone portions into a predetermined desired relationship and constraining relative motion of said adjacent bone portions in at least two dimensions.

13. The method according to claim 12, wherein said first and second adjacent bone portions form opposing bone portions of an articular joint and wherein said magnetic fields interact to reduce joint reactive forces while constraining the bone portions to at least approximate natural joint motion.

14. The method according to claim 12, wherein said first and second adjacent bone portions are opposite sides of a bone fracture and wherein said magnetic fields interact to stabilize said fracture.

* * * * *